US012569533B2

(12) United States Patent (10) Patent No.: US 12,569,533 B2
Widgerow et al. (45) Date of Patent: Mar. 10, 2026

(54) BRUISING AND FILLER COMPOSITIONS AND METHODS FOR USE

(71) Applicant: Alastin Skincare, Inc., Carlsbad, CA (US)

(72) Inventors: Alan David Widgerow, Carlsbad, CA (US); John A. Garruto, Carlsbad, CA (US)

(73) Assignee: Alastin Skincare, Inc., Carlsbad, CA (US)

( * ) Notice: Subject to any disclaimer, the term of this patent is extended or adjusted under 35 U.S.C. 154(b) by 253 days.

(21) Appl. No.: 18/405,561

(22) Filed: Jan. 5, 2024

(65) Prior Publication Data

US 2024/0180996 A1 Jun. 6, 2024

Related U.S. Application Data

(63) Continuation of application No. PCT/US2022/036363, filed on Jul. 7, 2022.

(60) Provisional application No. 63/219,664, filed on Jul. 8, 2021.

(51) Int. Cl.
| | |
|---|---|
| *A61K 38/06* | (2006.01) |
| *A61K 8/73* | (2006.01) |
| *A61K 9/00* | (2006.01) |
| *A61K 9/127* | (2025.01) |
| *A61K 31/685* | (2006.01) |
| *A61K 36/07* | (2006.01) |
| *A61K 38/07* | (2006.01) |
| *A61K 38/08* | (2019.01) |
| *A61K 38/40* | (2006.01) |
| *A61K 45/06* | (2006.01) |
| *A61Q 19/08* | (2006.01) |

(52) U.S. Cl.
CPC .............. *A61K 38/06* (2013.01); *A61K 8/735* (2013.01); *A61K 9/0014* (2013.01); *A61K 9/127* (2013.01); *A61K 31/685* (2013.01);

*A61K 36/07* (2013.01); *A61K 38/07* (2013.01); *A61K 38/08* (2013.01); *A61K 38/40* (2013.01); *A61K 45/06* (2013.01); *A61Q 19/08* (2013.01); *A61K 2800/91* (2013.01)

(58) Field of Classification Search
CPC ...... A61K 38/06; A61K 8/735; A61K 9/0014; A61K 9/127; A61K 31/685; A61K 36/07; A61K 38/07; A61K 38/08; A61K 38/40; A61K 45/06; A61K 2800/91; A61Q 19/08
See application file for complete search history.

(56) References Cited

U.S. PATENT DOCUMENTS

| | | | |
|---|---|---|---|
| 2014/0105959 A1 | 4/2014 | Paliwal et al. | |
| 2014/0302007 A1 | 10/2014 | Blanda et al. | |
| 2017/0224760 A1 | 8/2017 | Garruto et al. | |
| 2019/0038539 A1* | 2/2019 | Garruto ................... | A61K 8/64 |
| 2020/0046663 A1 | 2/2020 | Murdock et al. | |
| 2020/0069550 A1 | 3/2020 | Widgerow et al. | |

FOREIGN PATENT DOCUMENTS

WO WO-2020/227526 A1 11/2020

OTHER PUBLICATIONS

International Search Report and Written Opinion on PCT Appl. Ser. No. PCT/US2022/036363 dated Sep. 27, 2022 (16 pages).

* cited by examiner

*Primary Examiner* — Trevor Love

(74) *Attorney, Agent, or Firm* — Sunit Talapatra; Foley & Lardner LLP

(57) ABSTRACT

Compositions and methods for improving bruising, stimulating elastin and/or collagen production, stimulating intrinsic hyaluronic acid production, stimulating adipogenesis, reducing inflammation, or combinations thereof are provided herein. Compositions and methods described herein may be used in conjunction with use of a filler (e.g., a hyaluronic acid filler).

18 Claims, No Drawings

BRUISING AND FILLER COMPOSITIONS AND METHODS FOR USE

CROSS-REFERENCE TO RELATED APPLICATIONS

This application is a continuation of International Application No. PCT/US2022/036363 filed Jul. 7, 2022, which application claims priority under 35 U.S.C. § 119(e) to U.S. Provisional Application No. 63/219,664, filed Jul. 8, 2021, the entire contents of which are incorporated herein by reference.

BACKGROUND

A bruise may appear hours after injury to the tissues below the skin's surface or in some instances, a bruise appears instantly when a blood vessel is breached such as during the injection process, for example by the injection of a filler. Red blood cells extravasate into the surrounding tissue, and breakdown of these cells by macrophages results in loss of oxygen, giving the red blood cells a bluish hue. The byproducts of hemoglobin breakdown (heme, biliverdin, bilirubin, and hemosiderin) transmit the different colors to the skin that slowly resolve once these pigments are absorbed by the macrophages and digested. Due to the negative aesthetics of the skin discoloration that can occur for multiple days, there is a need for resolving the bruising process more quickly.

BRIEF SUMMARY

Described herein are compositions and methods for improving bruising. In some instances, the bruising is caused by an injection of a filler (e.g., hyaluronic acid filler). Compositions and methods as described herein can improve bruising by improving macrophage function. Compositions and methods as described herein may further stimulate elastin and/or collagen production, intrinsic hyaluronic acid production, adipogenesis, or reduce inflammation.

An aspect described herein are methods for improving bruising in a subject comprising applying to a body region or target area of the subject a topical composition comprising one or more ingredients encapsulated in a liposome, a tripeptide-1, and a hexapeptide-12, wherein the topical composition is administered or applied before injection of a filler comprising hyaluronic acid, after the injection of the filler, during the injection of the filler, or combinations thereof. In one feature, the topical composition is administered or applied at least 1 day prior to the injection of the filler. In one feature, the topical composition is administered or applied at least 1 week prior to the injection of the filler. In one feature, the topical composition is administered or applied at least 1 day after the injection of the filler. In one feature, the topical composition is administered or applied at least 1 week after the injection of the filler. In one feature, the topical composition is administered or applied 1, 2, 3, 4, 5, 6, 7, or 8 times a day. In one feature, the topical composition is administered or applied 4 times a day. In one feature, the body region comprises lips, mouth, cheek, chin, hands, temple, or periocular region. In one feature, the body region comprises an upper lip, lower lip, or both. In one feature, the target area comprises a wrinkle, an oral commissure, a marionette line, mandibular hollow, raise jowls, a frowning mouth, a pouty lower lip, a lateral expression line, a mental crease, a chin dimpling, a zygomatic hollow, a nasolabial fold, a tear trough, or a brow lift. In one feature, the subject is a human.

In one feature, the hyaluronic acid is a gel. In one feature, the hyaluronic acid (HA) is avian HA, bovine HA, non-animal stabilized HA, or combinations thereof. In one feature, the hyaluronic acid is generated by a *Streptococcus* species of bacteria. In one feature, the hyaluronic acid is chemically crosslinked with BDDE (1,4 butanediol diglycidyl ether). In one feature, the tripeptide-1 is present at 1-10 ppm. In one feature, the tripeptide-1 comprises palmitoyl tripeptide-1, myristoyl tripeptide-1, or a combination thereof. In one feature, the hexapeptide-12 comprises palmitoyl hexapeptide-12, myristoyl hexapeptide-12, or a combination thereof. In one feature, the hexapeptide-12 is present at 1-10 ppm. In one feature, a first ingredient of the one or more ingredients encapsulated in the liposome is hexapeptide-11. In one feature, the hexapeptide-11 is present at 50-150 ppm. In one feature, a second ingredient of the one or more ingredients encapsulated in the liposome is hexapeptide-38. In one feature, the hexapeptide-38 is acetyl hexapeptide-38. In one feature, the topical composition further comprises a tetrapeptide. In one feature, the tetrapeptide is tetrapeptide-2. In one feature, the topical composition further comprises phosphatidylserine. In one feature, the phosphatidylserine is present in a range of about 0.005 wt. % to about 0.1 wt. %. In one feature, the phosphatidylserine is present at no more than 5.0 wt %. In one feature, a third ingredient of the one or more ingredients encapsulated in the liposome is lactoferrin. In one feature, the lactoferrin is present in a range of about 0.005 wt. % to about 0.1 wt. %. In one feature, the lactoferrin is present at no more than 5.0 wt %. In one feature, the topical composition further comprises *Ledum palustre* extract, dill extract, *Tremella fuciformis* extract, butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, sodium hyaluronate crosspolymer, xylitylglucoside, anhydroxylitol, xylitol, hydroxymethoxyphenyl decanone, or combinations thereof. In one feature, the topical composition is aqueous.

An aspect described herein are methods for improving bruising in a subject comprising applying to a body region or target area of the subject a topical composition comprising one or more ingredients encapsulated in a liposome, wherein a first ingredient of the one or more ingredients encapsulated in the liposome is hexapeptide-11, a tripeptide-1, a hexapeptide-12, wherein the topical composition is administered or applied before injection of a filler comprising hyaluronic acid, after the injection of the filler, during the injection of the filler, or combinations thereof. In one feature, the topical composition is administered or applied at least 1 day prior to the injection of the filler. In one feature, the topical composition is administered or applied at least 1 week prior to the injection of the filler. In one feature, the topical composition is administered or applied at least 1 day after the injection of the filler. In one feature, the topical composition is administered or applied at least 1 week after the injection of the filler. In one feature, the topical composition is administered or applied 1, 2, 3, 4, 5, 6, 7, or 8 times a day. In one feature, the topical composition is administered or applied 4 times a day. In one feature, the body region comprises lips, mouth, cheek, chin, hands, temple, or periocular region. In one feature, the body region comprises an upper lip, lower lip, or both. In one feature, the target area comprises a wrinkle, an oral commissure, a marionette line, mandibular hollow, raise jowls, a frowning mouth, a pouty lower lip, a lateral expression line, a mental crease, a chin dimpling, a zygomatic hollow, a nasolabial fold, a tear trough, or a brow lift. In one feature, the subject is a human. In one feature, the hyaluronic acid is a gel. In one feature, the hyaluronic acid (HA) is avian HA, bovine HA, non-animal stabilized HA, or combinations thereof. In one feature, the hyaluronic acid is generated by a *Streptococcus* species of bacteria. In one feature, the hyaluronic acid is chemically crosslinked with BDDE (1,4 butanediol diglycidyl ether). In one feature, the tripeptide-1 is present at 1-10 ppm. In one feature, the tripeptide-1 comprises palmitoyl tripeptide-1, myristoyl tripeptide-1, or a combination thereof. In one feature, the hexapeptide-12 comprises palmitoyl hexapeptide-12, myristoyl hexapeptide-12, or a combination thereof. In one feature, the hexapeptide-12 is present at 1-10 ppm. In one feature, the hexapeptide-11 is present at 50-150 ppm. In one feature, a second ingredient of the one or more ingredients encapsulated in the liposome is hexapeptide-38. In one feature, the hexapeptide-38 is acetyl hexapeptide-38. In one feature, the topical composition further comprises a tetrapeptide. In one feature, the tetrapeptide is tetrapeptide-2. In one feature, the tetrapeptide-2 is acetyl tetrapeptide-2. In one feature, the topical composition further comprises phosphatidylserine. In one feature, the phosphatidylserine is present in a range of about 0.005 wt. % to about 0.1 wt. %. In one feature, the phosphatidylserine is present at no more than 5.0 wt. %. In one feature, a third ingredient of the one or more ingredients encapsulated in the liposome is lactoferrin. In one feature, the lactoferrin is present in a range of about 0.005 wt. % to about 0.1 wt. %. In one feature, the lactoferrin is present at no more than 5.0 wt. In one feature, the topical composition further comprises *Ledum palustre* extract, dill extract, *Tremella fuciformis* extract, butylene glycol, glycerin, squalane, *Dunaliella salina* extract, phospholipids, tocopherol, ascorbyl palmitate, xanthan gum, betaine, propanediol, lecithin, caprylic/ capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, sodium hyaluronate crosspolymer, xylitylglucoside, anhydroxylitol, xylitol, hydroxymethoxyphenyl decanone, or combinations thereof. In one feature, the topical composition is aqueous.

An aspect described herein are kits comprising: a first container comprising a topical composition, the topical composition comprising: one or more ingredients encapsulated in a liposome; a tripeptide-1; and a hexapeptide-12: a second container comprising a filler comprising hyaluronic acid; and instructions for use. In one feature, the topical composition is administered or applied at least 1 day prior to administration or application of the filler. In one feature, the topical composition is administered or applied at least 1 week prior to administration or application of the filler. In one feature, the topical composition is administered or applied at least 1 day after administration or application of the filler. In one feature, the topical composition is administered or applied at least 1 week after administration or application of the filler. In one feature, the topical composition is administered or applied 1, 2, 3, 4, 5, 6, 7, or 8 times a day. In one feature, the topical composition is administered or applied 4 times a day. In one feature, the hyaluronic acid is a gel. In one feature, the hyaluronic acid (HA) is avian HA, bovine HA, non-animal stabilized HA, or combinations thereof. In one feature, the hyaluronic acid is generated by a *Streptococcus* species of bacteria. In one feature, the hyaluronic acid is chemically crosslinked with BDDE (1,4 butanediol diglycidyl ether). In one feature, the tripeptide-1 is present at 1-10 ppm. In one feature, the tripeptide-1 comprises palmitoyl tripeptide-1, myristoyl tripeptide-1, or a combination thereof. In one feature, the hexapeptide-12 comprises palmitoyl hexapeptide-12, myristoyl hexapeptide-12, or a combination thereof. In one feature, the hexapeptide-12 is present at 1-10 ppm. In one feature, a first ingredient of the one or more ingredients encapsulated in the liposome is hexapeptide-11. In one feature, the hexapeptide-11 is present at 50-150 ppm. In one feature, a second ingredient of the one or more ingredients encapsulated in the liposome is hexapeptide-38. In one feature, the hexapeptide-38 is acetyl hexapeptide-38. In one feature, the kit further comprises a tetrapeptide. In one feature, the tetrapeptide is tetrapeptide-2. In one feature, the kit further comprises phosphatidylserine. In one feature, the phosphatidylserine is present in a range of about 0.005 wt. % to about 0.1 wt. %. In one feature, the phosphatidylserine is present at no more than 5.0 wt %. In one feature, a third ingredient of the one or more ingredients encapsulated in the liposome is lactoferrin. In one feature, the lactoferrin is present in a range of about 0.005 wt. % to about 0.1 wt. %. In one feature, the lactoferrin is present at no more than 5.0 wt %. In one feature, the kit further comprises *Ledum palustre* extract, dill extract, *Tremella fuciformis* extract, butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, sodium hyaluronate crosspolymer, xylitylglucoside, anhydroxylitol, xylitol, hydroxymethoxyphenyl decanone, or combinations thereof. In one feature, the topical composition is aqueous.

An aspect described herein are kits comprising: a first container comprising a topical composition, the topical composition comprising: one or more ingredients encapsulated in a liposome, wherein a first ingredient of the one or more ingredients encapsulated in the liposome is hexapeptide-11; a tripeptide-1; and a hexapeptide-12: a second container comprising a filler comprising hyaluronic acid; and instructions for use. In one feature, the topical composition is administered or applied at least 1 day prior to administration or application of the filler. In one feature, the topical composition is administered or applied at least 1 week prior to administration or application of the filler. In one feature, the topical composition is administered or applied at least 1 day after administration or application of the filler. In one feature, the topical composition is administered or applied at least 1 week after administration or application of the filler. In one feature, the topical composition is administered or applied 1, 2, 3, 4, 5, 6, 7, or 8 times a day. In one feature, the topical composition is administered or applied 4 times a day. In one feature, the hyaluronic acid is a gel. In one feature, the hyaluronic acid (HA) is avian HA, bovine HA, non-animal stabilized HA, or combinations thereof. In one feature, the hyaluronic acid is generated by a *Streptococcus* species of bacteria. In one feature, the hyaluronic acid is chemically crosslinked with BDDE (1,4 butanediol diglycidyl ether). In one feature, the tripeptide-1 is present at 1-10 ppm. In one feature, the tripeptide-1 comprises palmitoyl tripeptide-1, myristoyl tripeptide-1, or a combination thereof. In one feature, the hexapeptide-12 comprises palmitoyl hexapeptide-12, myristoyl hexapeptide-12, or a combination thereof. In one feature, the hexapeptide-12 is present at 1-10 ppm. In one feature, the hexapeptide-11 is present at 50-150 ppm. In one feature, a second ingredient of the one or more ingredients encapsulated in the liposome is hexapeptide-38. In one feature, the hexapeptide-38 is acetyl hexapeptide-38. In one feature, the kit further comprises a tetrapeptide. In one feature, the tetrapeptide is tetrapeptide-2. In one feature, the tetrapeptide-2 is acetyl tetrapeptide-2. In one feature, the kit further comprises phosphatidylserine. In one feature, the phosphatidylserine is present in a range of about 0.005 wt. % to about 0.1 wt. %. In one feature, the phosphatidylserine is present at no more than 5.0 wt. %. In one feature, a third ingredient of the one or more ingredients encapsulated in the liposome is lactoferrin. In one feature, the lactoferrin is present in a range of about 0.005 wt. % to about 0.1 wt. %. In one feature, the lactoferrin is present at no more than 5.0 wt. In one feature, the kit further comprises *Ledum palustre* extract, dill extract, *Tremella fuciformis* extract, butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, sodium hyaluronate crosspolymer, xylitylglucoside, anhydroxylitol, xylitol, hydroxymethoxyphenyl decanone, or combinations thereof. In one feature, the topical composition is aqueous.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Compositions for Improving Bruising

A bruise is caused by bleeding under the skin due to trauma to capillaries under the skin. Trauma can be caused by a cosmetic procedure such as an injection of a filler (e.g., a hyaluronic acid filler). As a result of the trauma, there can be an extravasation of blood to the surrounding tissue. Generally, bruising results in a visible discoloration on the skin. The discoloration caused by bruising can take days to disappear and is resolved through the function of macrophages. Accordingly, compositions are needed for improving the bruising process.

Described herein are compositions and methods for improving bruising. Compositions and methods as described herein can improve bruising by improving macrophage function. Compositions and methods as described herein may further stimulate elastin and/or collagen production, intrinsic hyaluronic acid production, adipogenesis, or reduce inflammation.

Liposomes

Described herein are liposomal compositions for improved distribution, efficacy, bioavailability, and/or activity. Liposomal compositions may improve distribution, efficacy, bioavailability, and/or activity of the active ingredient by improving delivery and tissue (e.g. skin) penetration. In some instances, improved delivery and skin penetration result from the active ingredient being incorporated (e.g. encapsulated) in a liposome. In some instances, the active ingredient is a peptide that is encapsulated in a liposome.

Liposomal compositions as described herein may comprise a peptide encapsulated in a liposome. In some embodiments, the peptide is tripeptide-1. In some embodiments, the peptide is hexapeptide-12. In some embodiments, the peptide is hexapeptide-11 In some embodiments, the peptide is hexapeptide-38. In some embodiments, the peptide is tetrapeptide-2. In some embodiments, the peptide is functionalized with a palmitoyl group. In some embodiments, the peptide is functionalized with an acetyl group. For example, the peptide is acetyl hexapeptide-38.

Liposomal compositions as described herein may comprise various ingredients encapsulated in a liposome. In some embodiments, the ingredient is lactoferrin. In some embodiments, the ingredient is phosphatidylserine. In some embodiments, the ingredient is *Ledum Palustre* extract. In some embodiments, the ingredient is *Arnica Montana* extract. In some embodiments, the ingredient is sodium hyaluronate. In some embodiments, the ingredient is larger than 50 kDa.

Lecithin and other phospholipids may be used to prepare liposomes containing the peptide compositions as described herein. In some embodiments, liposomes are used to prepare one or more peptides. In some embodiments, the peptide is functionalized with an acetyl group. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the peptide compositions as described herein.

The phospholipids used to prepare the liposomal compositions described herein may comprise a transition phase temperature of about 10° C. to about 25° C. In some instances, the phospholipids comprise a transition phase temperature of about 10° C., 12° C., 14° C., 16° C., 18° C., 20° C., 22° C., 24° C., 26° C., 28° C., 30° C., 32° C., 34° C., 36° C., 38° C., 40° C., or more than 40° C. In some instances, the phospholipids comprise a transition phase temperature in a range of about 10° C. to about 40° C., about 12° C. to about 36° C., about 14° C. to about 32° C., about 16° C. to about 20° C., or about 21° C. to about 25° C.

The topical composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting composition contains micelles, i.e., spherical oil droplets.

The liposomal composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Described herein, in some embodiments, are methods for preparing a composition comprising a peptide encapsulated in a liposome, comprising: combining the peptide and a solvent to form a mixture; and contacting the mixture with an aqueous solution comprising liposomes. In some instances, the contacting occurs at a temperature between about 10° C. and about 25° C. In some instances, the contacting occurs at a temperature of about 10° C., 12° C., 14° C., 16° C., 18° C., 20° C., 22° C., 24° C., 26° C., 28° C., 30° C., 32° C., 34° C., 36° C., 38° C., 40° C., or more than 40° C. In some instances, the contacting occurs at a temperature in a range of about 10° C. to about 40° C., about 12° C. to about 36° C., about 14° C. to about 32° C., about 16° C. to about 20° C., or about 21° C. to about 25° C.

Methods for preparing a composition comprising a peptide encapsulated in a liposome may comprise use of a solvent. In some instances, the solvent is water. In some instances, the solvent is an organic solvent. Exemplary organic solvents include, but are not limited to, petroleum ether, cyclohexane, toluene, carbon tetrachloride, dichloromethane, chloroform, diethyl ether, diisopropyl ether, ethyl acetate, butanol, n-propanol, ethanol, methanol, polyethylene glycol, propylene glycol, and pyridine. In some instances, the solvent is a glycol. In some instances, the solvent is butylene glycol. In some instances, the solvent is caprylyl glycol. In some instances, the solvent is propanediol (propylene glycol).

The solvent may be used at various percentages. In some instances, the solvent is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10%. The solvent may be propanediol, butylene glycol, or caprylyl glycol.

Methods as described herein, in some embodiments, comprises combining the peptide and a solvent to form a mixture; and contacting the mixture with an aqueous solution comprising liposomes, wherein the aqueous solution comprises a percentage of water and a percentage of liposomes. In some instances, the aqueous solution comprises at least or about 20%, 30%, 40%, 50%, 60%, 70%, 80%, 90%, or more than 90% water. In some instances, the aqueous solution comprises water in a range of about 10% to about 95%, about 20% to about 90%, about 30% to about 85%, about 40% to about 80%, or about 50% to about 60%. In some instances, the aqueous solution comprises at least or about 20%, 30%, 40%, 50%, 60%, or more than 60% liposomes. In some instances, the aqueous solution comprises liposomes in a range of about 10% to about 80%, about 20% to about 70%, or about 30% to about 60%. A ratio of liposomes to water may be in a range of about 1:9 to about 3:7. In some instances, the ratio of liposomes to water may be at least or about 1:10, 1:9, 1:8, 1:7, 1:6, 1:5, 1:4, 1:3, or 1:2.

Methods for generation of liposomal compositions as described herein may result in an entrapment efficacy of no more than 100%. In some instances, the entrapment efficacy is no more than 50%, 60%, 70%, 80%, 90%, 95%, 99%, or 99.5%.

Described herein are liposomal compositions, wherein the peptide comprises a percentage of the composition. In some embodiments, the peptide is provided at least or about 0.0001%, 0.0005%, 0.00055%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% of the composition. In some embodiments, the peptide is provided at least or about 10%, 11%, 12%, 13%, 14%, 15%, 16%, 17%, 18%, 19%, 20%, 22%, 24%, 26%, 28%, 30% or more than 30% of the composition. In some embodiments, the peptide is provided in a range of about 0.001% to about 6%, about 0.002% to about 4%, about 0.01% to about 5%, or about 0.02% to about 2% by weight. In some embodiments, the peptide is provided at about 0.03% of the composition.

Described herein are liposomal compositions, wherein the liposomes comprise a percentage of the composition. In some embodiments, the liposomes are provided at least or about 10%, 11%, 12%, 13%, 14%, 15%, 16%, 17%, 18%, 19%, 20%, 22%, 24%, 26%, 28%, 30% or more than 30% of the composition. In some embodiments, the liposomes are provided in a range of about 5% to about 90%, about 10% to about 80%, about 20% to about 70%, about 30% to about 60%, about 10% to about 30%, or about 20% to about 40%. In some embodiments, the liposomes are provided at about 30%. In some embodiments, the liposomes are provided at 27%.

Liposomal compositions as described herein, in some embodiments, comprise an average particle size of at most 220 nanometers (nm). In some instances, the average particle size is at most 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 230 nm, 240 nm, 250 nm, 260 nm, 270 nm, 280 nm, 290 nm, 300 nm, 320 nm, 340 nm, 360 nm, 380 nm, or 400 nm. In some instances, the average particle size is about 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 230 nm, 240 nm, 250 nm, 260 nm, 270 nm, 280 nm, 290 nm, 300 nm, 320 nm, 340 nm, 360 nm, 380 nm, or 400 nm. In some instances, the average particle size is in a range of about 50 nm to about 500 nm, about 100 nm to about 400 nm, about 150 nm to about 220 nm, about 180 nm to about 220 nm, or about 190 nm to about 210 nm.

In some instances, the liposomal compositions comprise an active agent that has a molecular weight of no more than about 600 Daltons (Da). In some instances, the active agent has a molecular weight of at least or about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more than 1000 Daltons (Da). In some instances, the active agent has a molecular weight of at least or about 1000, 1100, 1200, 1300, 1400, 1500, 1600, 1700, 1800, 1900, 2000, 2100, 2200, 2300, 2400, 2500, 2600, 2700, 2800, 2900, 3000, 4000, 5000, 6000, or more than 6000 Daltons (Da). In some instances, the active agent has a molecular weight in a range of about 50 to about 1000, about 100 to about 900, about 200 to about 800, about 300 to about 700, or about 400 to about 600 Daltons (Da). In some instances, the active agent is a peptide. In some instances, the active agent is a peptide encapsulated in a liposome.

A polydispersity index (PdI) of a liposomal composition as described herein, in some embodiments, is in a range of 0 to about 0.2. In some instances, the polydispersity index is about 0.01, 0.025, 0.05, 0.1, 0.25, 0.3, 0.35, 0.4, 0.45, 0.5, 0.55, 0.6, 0.65, 0.7, 0.75, or 0.8. In some instances, the polydispersity index is in a range of about 0.01 to about 0.8, about 0.025 to about 0.75, about 0.05 to about 0.6, or about 0.1 to about 0.3.

In some instances, an intercept of a liposomal composition as described herein is in a range of about 0.85 to about 0.95. In some instances, the intercept is the amplitude. In some instances, the intercept is at least or about 0.65, 0.70, 0.75, 0.80, 0.85, 0.90, or 0.95.

In some embodiments, the liposomes comprise propanediol, lecithin, or a combination thereof. In some embodiments, the propanediol is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol is provided in a range of about 0.001% to about 6%, about 0.002% to about 4%, about 0.01% to about 3%, or about 0.02% to about 2% by weight. In some embodiments, the lecithin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the lecithin is provided in a range of about 0.001% to about 6%, about 0.002% to about 4%, about 0.01% to about 3%, or about 0.02% to about 2% by weight. In some embodiments, the liposomes comprise propanediol and lecithin. In some embodiments, the propanediol and lecithin are provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol and lecithin are provided in a range of about 0.001% to about 6%, about 0.002% to about 4%, about 0.01% to about 3%, or about 0.02% to about 2% by weight. In some embodiments, the propanediol and lecithin are provided at about 0.90% by weight Described herein are liposomal compositions comprising improved distribution, efficacy, bioavailability, and/or activity. The liposomal compositions may comprise improved distribution, efficacy, bioavailability, and/or activity as compared to compositions not comprising liposomes. In some instances, the distribution is improved by at least or about 0.5x, 1.0x, 1.5x, 2.0x, 2.5x, 3.0x, 4.0x, 4.5x, 5x, or more than 5x as compared to compositions not comprising liposomes. In some instances, the efficacy is improved by at least or about 0.5x, 1.0x, 1.5x, 2.0x, 2.5x, 3.0x, 4.0x, 4.5x, 5x, or more than 5x as compared to compositions not comprising liposomes. In some instances, the bioavailability is improved by at least or about 0.5x, 1.0x, 1.5x, 2.0x, 2.5x, 3.0x, 4.0x, 4.5x, 5x, or more than 5x as compared to compositions not comprising liposomes. In some instances, the activity is improved by at least or about 0.5x, 1.0x, 1.5x, 2.0x, 2.5x, 3.0x, 4.0x, 4.5x, 5x, or more than 5x as compared to compositions not comprising liposomes. The distribution, efficacy, bioavailability, and/or activity may be improved by at least or about 10%, 15%, 20%, 25%, 30%, 35%, 40%, 45%, 50%, 55%, 60%, 65%, 70%, 75%, 80%, 85%, 90%, or more than 90% as compared to compositions not comprising liposomes.

Liposomal compositions and methods as described herein, in some embodiments, are topical compositions. In some instances, the liposomal compositions are oil free. In some instances, the liposomal compositions are preservative free. In some embodiments, the liposomal formulation is an aqueous formulation. In some embodiments, the liposomal formulation is an anhydrous formulation. In some instances, the liposomal composition comprises a pH in a range of about 5 to about 8. In some instances, the liposomal composition comprises a pH of at least or about 2, 3, 4, 5, 6, 7, 8, 9, or 10.

Methods and compositions as described herein may result in improved follicular penetration. In some instances, the follicular penetration is improved by at least or about 0.5x, 1.0x, 1.5x, 2.0x, 2.5x, 3.0x, 4.0x, 4.5x, 5x, or more than 5x. The follicular penetration may be improved by at least or about 10%, 15%, 20%, 25%, 30%, 35%, 40%, 45%, 50%, 55%, 60%, 65%, 70%, 75%, 80%, 85%, 90%, or more than 90%. In some instances, compositions result in follicular penetration of a depth of at least or about 0.5, 0.75, 1, 1.25, 1.5, 2, 2.5, 3, 3.5, 4, 4.5, 5, 5.5, 6, 7, 8, 9, 10, or more than 10 millimeters.

Peptides

Peptides as described herein, in some embodiments, improve bruising, elastin and/or collagen simulation, hyaluronic acid stimulation, adipocyte stimulation, reduce inflammation, or combinations thereof. In some embodiments, peptides as described herein improve macrophage function. In some embodiments, tripeptide-1 results in elastin and/or collagen stimulation, extracellular matrix (ECM) recycling, anti-inflammatory effects, or combinations thereof. In some embodiments, hexapeptide-12 draws in newly produced elastin. In some embodiments, acetyl tetrapeptide-2 stimulates fibroblasts to produce elastin.

Peptides as described herein, in some embodiments, in combination improve bruising, elastin and/or collagen simulation, hyaluronic acid stimulation, adipocyte stimulation, reduce inflammation, or combinations thereof. For example, tripeptide-1 and hexapeptide-12 improve macrophage function. In some embodiments, tripeptide-1 and hexapeptide-11 improve macrophage function. In some embodiments, tripeptide-1, hexapeptide-11, and hexapeptide-12 improve macrophage function. For example, hexapeptide-11 in combination with one or more different peptides such as tripeptide-1, hexapeptide-12, or a combination thereof is a potent stimulator of autophagy and macrophage clustering and can improve removal of hemosiderin pigment associated with bruising and bleeding.

Compositions as described herein comprise a varying concentration of peptide. In some instances, a peptide is present at about 50 ppm or less to 1000, 5000, 10000, 50000, 100000, 500000 ppm or more, e.g., 100 ppm of the peptide. In some instances, a peptide is present at about 1, 2, 3, 4, 5, 6, 7, 8, 9, 10, 15, 20, 25, 50, 75, 100, 200, 300, 400, 500, 600, 700, 800, 900, 1000, or more than 1000 ppm. In some instances, a peptide is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 ppm. In some instances, a peptide is present at about 1, 2, 3, 4, 5, 6, 7, 8, 9, 10, 15, 20, 25, 50, 75, 100, 200, 300, 400, 500, 600, 700, 800, 900, 1000, or more than 1000 microgram per milliliter (ug/mL). In some instances, a peptide is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 microgram per milliliter. In some instances, a peptide is present from about 0.01% to about 10%, about 0.01% to about 0.02%, about 0.01% to about 0.03%, about 0.01% to about 0.04%, about 0.01% to about 0.05%, about 0.01% to about 0.1%, about 1% to about 5%, or about 1% to about 10% by weight (wt. %).

Compositions as described herein, in some embodiments, comprise a plurality of peptides. In some instances, a peptide of the plurality of peptides is present at about 50 ppm or less to 1000, 5000, 10000, 50000, 100000, 500000 ppm or more, e.g., 100 ppm of the peptide, or any other suitable amount. In some instances, a peptide of the plurality of peptides is present at about 1, 2, 3, 4, 5, 6, 7, 8, 9, 10, 15, 20, 25, 50, 75, 100, 200, 300, 400, 500, 600, 700, 800, 900, 1000, or more than 1000 ppm. In some instances, a peptide of the plurality of peptides is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 ppm. In some instances, a peptide of the plurality of peptides is present at about 1, 2, 3, 4, 5, 6, 7, 8, 9, 10, 15, 20, 25, 50, 75, 100, 200, 300, 400, 500, 600, 700, 800, 900, 1000, or more than 1000 microgram per milliliter (ug/mL). In some instances, a peptide of the plurality of peptides is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 microgram per milliliter. In some instances, a peptide of the plurality of peptides is present from about 0.01% to about 10%, about 0.01% to about 0.02%, about 0.01% to about 0.03%, about 0.01% to about 0.04%, about 0.01% to about 0.05%, about 0.01% to about 0.1%, about 1% to about 5%, or about 1% to about 10% by weight (wt. %). In some embodiments, a peptide of the plurality of peptides is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, a peptide of the plurality of peptides is provided in a range of about 0.25% to about 10%, about 0.5% to about 8%, about 0.75% to about 6%, or about 1% to about 4% by weight. In some embodiments, each peptide of the plurality of peptides is provided in a range of about 0.001% to about 6%, about 0.002% to about 4%, about 0.01% to about 3%, or about 0.02% to about 2% by weight.

In some embodiments, the peptide is tripeptide-1, hexapeptide-12, hexapeptide-11, hexapeptide-38, tetrapeptide-2, or combinations thereof.

In some embodiments, the tripeptide-1 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the tripeptide-1 is provided in a range of about 0.25% to about 10%, about 0.5% to about 8%, about 0.75% to about 6%, or about 1% to about 4% by weight. In some embodiments, the tripeptide-1 is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the tripeptide-1 is provided in a range of about 0.25 to about 10, about 0.5 to about 8, about 1 to about 6, or about 2 to about 4 ppm. In some embodiments, the tripeptide-1 is provided in a range of about 1 to about 10 ppm. In some embodiments, the tripeptide-1 is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the tripeptide-1 is provided in a range of about 0.25 to about 10, about 0.5 to about 8, about 1 to about 6, or about 2 to about 4 microgram per milliliter.

In some embodiments, the hexapeptide-12 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the hexapeptide-12 is provided in a range of about 0.25% to about 10%, about 0.5% to about 8%, about 0.75% to about 6%, or about 1% to about 4% by weight. In some embodiments, the hexapeptide-12 is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the hexapeptide-12 is provided in a range of about 1 to about 10 ppm. In some embodiments, the hexapeptide-12 is provided in a range of about 0.25 to about 10, about 0.5 to about 8, about 1 to about 6, or about 2 to about 4 ppm. In some embodiments, the hexapeptide-12 is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the hexapeptide-12 is provided in a range of about 0.25 to about 10, about 0.5 to about 8, about 1 to about 6, or about 2 to about 4 microgram per milliliter.

In some embodiments, the hexapeptide-11 is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%1, 1.5%, 2.0%, 2.5%, 3.0%, 3.5%, 4.0%, 4.5%, 5.0%, 5.5%, 6.0%, 6.5%, 7.0%, 8%, 9%, 10%, 20%, 30%, 40%, 50%, 60%, 70%, 80%, 90% or more than 90% by weight (wt. %). In some embodiments, the hexapeptide-11 is provided in a range of about 0.25% to about 10%, about 0.5% to about 8%, about 0.75% to about 6%, or about 1% to about 4% by weight. In some embodiments, the hexapeptide-11 is provided in a range of about 0.001% to about 6%, about 0.002% to about 4%, about 0.01% to about 3%, or about 0.02% to about 2%. In some embodiments, the hexapeptide-11 is provided in a range of about 0.005% to about 0.02% by weight. In some embodiments, the hexapeptide-11 is provided at least or about 5, 10, 20, 25, 50, 75, 100, 150, 200, 250, or more than 250 ppm. In some embodiments, the hexapeptide-11 is provided in a range of about 25 to about 250, about 50 to about 200, or about 75 to about 150 ppm. In some embodiments, the hexapeptide-11 is provided in a range of about 10 to about 100 ppm. In some embodiments, the hexapeptide-11 is provided at least or about 5, 10, 20, 25, 50, 75, 100, 150, 200, 250, or more than 250 microgram per milliliter (ug/mL). In some embodiments, the hexapeptide-11 is provided in a range of about 25 to about 250, about 50 to about 200, or about 75 to about 150 microgram per milliliter.

In some embodiments, the hexapeptide-38 is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, 20%, 30%, 40%, 50%, 60%, 70%, 80%, 90% or more than 90% by weight (wt. %). In some embodiments, the hexapeptide-38 is provided in a range of about 0.25% to about 10%, about 0.5% to about 8%, about 0.75% to about 6%, or about 1% to about 4% by weight. In some embodiments, the hexapeptide-38 is provided in a range of about 0.001% to about 6%, about 0.002% to about 4%, about 0.01% to about 3%, or about 0.02% to about 2%. In some embodiments, the hexapeptide-38 is provided in a range of about 0.005% to about 0.02% by weight. In some embodiments, the hexapeptide-38 is provided at least or about 0.25, 0.5, 0.75, 1, 1.5, 2, 2.5, 3, 3.5, 4, 5, 10, 20, 25, 50, 75, 100, 150, 200, 250, or more than 250 ppm. In some embodiments, the hexapeptide-38 is provided in a range of about 25 to about 250, about 50 to about 200, or about 75 to about 150 ppm. In some embodiments, the hexapeptide-38 is provided at least or about 5, 10, 20, 25, 50, 75, 100, 150, 200, 250, or more than 250 microgram per milliliter (ug/mL). In some embodiments, the hexapeptide-38 is provided in a range of about 25 to about 250, about 50 to about 200, or about 75 to about 150 microgram per milliliter. In some embodiments, the hexapeptide-38 is acetyl hexapeptide-38.

In some embodiments, the tetrapeptide-2 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the tetrapeptide-2 is provided in a range of about 0.25% to about 10%, about 0.5% to about 8%, about 0.75% to about 6%, or about 1% to about 4% by weight. In some embodiments, the tetrapeptide-2 is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the tetrapeptide-2 is provided in a range of about 0.25 to about 10, about 0.5 to about 8, about 1 to about 6, or about 2 to about 4 ppm. In some embodiments, the tetrapeptide-2 is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the tetrapeptide-2 is provided in a range of about 0.25 to about 10, about 0.5 to about 8, about 1 to about 6, or about 2 to about 4 microgram per milliliter.

In example embodiments, a weight ratio for the first peptide to the second peptide in a topical composition is 1 part first peptide to 0.2 to 10 parts second peptide, 1 to 10 parts second peptide, 1 to 8 parts second peptide, or 1 to 5.5 parts second peptide. The following nomenclature is employed herein to refer to various amino acids: Alanine (also referred to herein as "Ala" or "A"), Arginine (also referred to herein as "Arg" or "R"), Asparagine (also referred to herein as "Asn" or "N"), Aspartic acid (also referred to herein as "Asp" or "D"), Cysteine (also referred to herein as "Cys" or "C"), Glutamic acid (also referred to herein as "Glu" or "E"), Glutamine (also referred to herein as "Gln" or "Q"), Glycine (also referred to herein as "Gly" or "G"), Histidine (also referred to herein as "His" or "H"), Isoleucine (also referred to herein as "Ile" or "I"), Leucine (also referred to herein as "Leu" or "L"), Lysine (also referred to herein as "Lys" or "K"), Methionine (also referred to herein as "Met" or "M"), Phenylalanine (also referred to herein as "Phe" or "F"), Proline (also referred to herein as "Pro" or "P"), Serine (also referred to herein as "Ser" or "S"), Threonine (also referred to herein as "Thr" or "T"), Tryptophan (also referred to herein as "Trp" or "W"), Tyrosine (also referred to herein as "Tyr" or "Y"), Valine (also referred to herein as "Val" or "V").

In some embodiments, the first peptide is a dipeptide. Suitable dipeptides include but are not limited to those having the following sequence of amino acids: KK, KP, CK, KC, KT, DF, NF, VW, YR, or TT. In some embodiments, the dipeptide has the following amino acid sequence: KV. In other embodiments, the first peptide is a tripeptide. Suitable tripeptides include but are not limited to those having the following sequence of amino acids: HGG, RKR, GHK, GKH, GGH, GHG, KFK, or KPK. In some embodiments, the tripeptide has the following amino acid sequence: KVK. In some embodiments, the first peptide is a tetrapeptide. Suitable tetrapeptides include but are not limited to those having the following sequence of amino acids: GQPR, KTFK, AQTR, or RSRK. In some embodiments, the tetrapeptide has the following sequence of amino acids: KDVY. In some embodiments, the second peptide is a pentapeptide. Suitable pentapeptides include but are not limited to those having the following sequence of amino acids: KTTKS, YGGFX, or KLAAK. In some embodiments, the second peptide is a hexapeptide. Suitable hexapeptides include but are not limited to those having the following sequence of amino acids: VGVAPG or GKTTKS. In some embodiments, the hexapeptide has the following sequence of amino acids: FVAPFP. In some embodiments, the second peptide is a heptapeptide. Suitable heptapeptides include but are not limited to one having an amino acid sequence RGYYLLE, or Heptapeptide-6 (a pro-sirtuin peptide). The compositions may include two or more peptides, e.g., two dipeptides and one pentapeptide; one tripeptide and one hexapeptide; one dipeptide, one tripeptide, and one heptapeptide, or the like, provided that the composition contains at least one dipeptide, tripeptide, or tetrapeptide and at least one pentapeptide, hexapeptide, or heptapeptide. In some embodiments, the compositions comprise a tripeptide and one or more hexapeptides. In some embodiments, the compositions comprise a tripeptide, one or more hexapeptides, and a tetrapeptide. In some embodiments, the tripeptide is tripeptide-1. In some embodiments, the one or more hexapeptide is hexapeptide-12. In some embodiments, the one or more hexapeptide is hexapeptide-11. In some embodiments, the one or more hexapeptide is hexapeptide-38. In some embodiments, the compositions comprise tripeptide-1, hexapeptide-12, hexapeptide-11, and hexapeptide-38. In some embodiments, the tetrapeptide is tetrapeptide-2.

The peptide can be functionalized. For example, the peptide can be functionalized with a fatty acid, e.g., myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, or the like. Examples include palmitoyl hexapeptide-12 (Pal-VGVAPG), palmitoyl tripeptide-1 (Pal-GHK), myristoyl hexapeptide-12 (Myr-VGVAPG), and myristoyl tripeptide-1 (Myr-GHK). Palmitoyl or myristoyl functionalization can be desirable in certain embodiments as it exhibits enhanced penetration when compared to other fatty acids. In some embodiments, the peptide is functionalized with a chemical group. For example, the peptide is functionalized with acetyl. Examples include acetyl hexapeptide-38 and acetyl tetrapeptide-2. In some instances, the peptide is functionalized with a functional group comprising no more than 14 carbons. In some instances, the peptide is functionalized with a functional group comprising no more than 3, 4, 5, 6, 7, 8, 9, 10, 11, 12, 13, 14, 15, 16, 17, 18, 19, 20, or more than 20 carbons. In some instances, the peptide is non-palmitoylated. Without wishing to be limited to a particular theory, incorporation of the peptide in a liposome, in some embodiments, increases the lipophilicity of a peptide that is functionalized or is not functionalized.

Some embodiments of the methods and compositions provided herein include as a first peptide glycine-histidine-lysine (GHK). GHK is a peptide sequence that is rarely found in the class of proteins in general, but is frequently found in extracellular matrix proteins. The small size of GHK permits it to approach membrane receptors far more easily than larger peptides. Further, its unique, copper-binding structure enhances copper transport into and out of cells and promotes wound healing through several different but related pathways. Due to its strong copper binding structure, GHK can be provided in the form of GHK-Cu (copper-bound GHK form).

In compositions, the tripeptide is typically present in an amount of from about 50 ppm or less to about 100, 200, 300, 400, or 500 ppm or more, e.g., 50 ppm to 150 ppm.

In compositions, the hexapeptide is typically present in an amount of from about 50 ppm or less to about 100, 200, 300, 400, or 500 ppm or more, e.g., 50 ppm to 150 ppm.

In compositions, the tetrapeptide is typically present in an amount of from about 50 ppm or less to about 100, 200, 300, 400, or 500 ppm or more, e.g., 50 ppm to 150 ppm.

The peptides can advantageously be provided in a base for suitable for combining with other components of a liposomal composition. The base can include one or more components such as a thickener/binding agent (e.g., pentaerythrityl tetraisostearate), an emollient/dispersing agent (e.g., caprylic/capric triglyceride), a solvent (e.g., propylene carbonate), and/or a rheology modifier/antisettling agent (e.g., disteardimonium hectorite).

Phosphatidylserine

Compositions as described herein, in some embodiments, comprise phosphatidylserine. Exposure of phosphatidylserine from the inner cell membrane of red blood cells can induce phagocytosis of red blood cells. See Chang C F, Goods B A, Askenase M H, et al. Erythrocyte efferocytosis modulates macrophages towards recovery after intracerebral hemorrhage. *The Journal of clinical investigation.* 2018; 128(2):607-624.

In some embodiments, phosphatidylserine is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the phosphatidylserine is provided in a range of about 0.25% to about 10%, about 0.5% to about 8%, about 0.75% to about 6%, or about 1% to about 4% by weight. In some embodiments, the phosphatidylserine is provided in a range of about 0.001% to about 6%, about 0.002% to about 4%, about 0.005% to about 0.1%, about 0.01% to about 3%, or about 0.02% to about 2% by weight. In some embodiments, the phosphatidylserine is provided in a range of about 0.005% to about 0.02% by weight. In some embodiments, the phosphatidylserine is provided at about 0.05% by weight. In some embodiments, the phosphatidylserine is provided at about 0.25% by weight. In some embodiments, the phosphatidylserine is provided at about 1% by weight. In some embodiments, the phosphatidylserine is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the phosphatidylserine is provided in a range of about 5 to about 1000, about 10 to about 900, about 30 to about 800, about 50 to about 700, about 60 to about 600, or about 100 to about 500 microgram per milliliter (ug/mL).

*Arnica Montana* Extract

Compositions as described herein, in some embodiments, comprise an anti-inflammatory agent. Exemplary anti-inflammatory agents include, but are not limited to, *Arnica montana* extract. *Arnica montana* extract includes components such as essential oils, fatty acids, thymol, pseudoguaianolide sesquiterpene lactones, flavanone glycosides, flavonoids, and coumarins. It can exhibit an anti-inflammatory effect. In some instances, *Arnica montana* extract accelerates healing, reduces bruising potential, modulates inflammation, and stimulates granular tissue and accelerates healing, or combinations thereof. See Rajasingh J, Marzotto M, Bonafini C, et al. *Arnica montana* Stimulates Extracellular Matrix Gene Expression in a Macrophage Cell Line Differentiated to Wound-Healing Phenotype. *PloS one.* 2016; 11(11). In some instances, *Arnica montana* improves bruising by decreasing the inflammation associated with blood products. In some instances, *Arnica montana* stimulates the function of M2 macrophages and improves wound healing. See Rajasingh J, Marzotto M, Bonafini C, et al. *Arnica montana* Stimulates Extracellular Matrix Gene Expression in a Macrophage Cell Line Differentiated to Wound-Healing Phenotype. *PloS one.* 2016;11(11).

In some embodiments, *Arnica montana* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 5%, 6%, 7%, 8%, 9%, 10%, or more than 10% by weight (wt. %). In some embodiments, the *Arnica montana* extract is provided in a range of about 0.25% to about 10%, about 0.5% to about 8%, about 0.75% to about 6%, or about 1% to about 4% by weight. In some embodiments, the *Arnica montana* extract is provided in a range of about 0.001% to about 6%, about 0.002% to about 4%, about 0.01% to about 3%, about 0.02% to about 2% by weight, or about 0.1% to about 2.5%.

*Ledum Palustre*

Compositions as described herein, in some embodiments, comprise *Ledum palustre* extract. *Ledum palustre* is also known as marsh tea, wild rosemary, or labrador tea. *Ledum palustre* has been used for insect bites, puncture wounds, and cold swellings or bruises. See Kang J Y, Tran K D, Seiff S R, Mack W P, Lee W W. Assessing the Effectiveness of *Arnica montana* and *Rhododendron tomentosum* (*Ledum palustre*) in the Reduction of Ecchymosis and Edema After Oculofacial Surgery: Preliminary Results. *Ophthalmic Plast Reconstr Surg.* 2017; 33(1):47-52.

In some embodiments, *Ledum palustre* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the *Ledum palustre* extract is provided in a range of about 0.25% to about 10%, about 0.5% to about 8%, about 0.75% to about 6%, or about 1% to about 4% by weight. In some embodiments, the *Ledum palustre* extract is provided in a range of about 0.001% to about 6%, about 0.002% to about 4%, about 0.01% to about 3%, about 0.02% to about 2% by weight, or about 0.1% to about 2.5%. In some embodiments, the *Ledum palustre* extract is provided at about 0.25%. In some embodiments, the *Ledum palustre* extract is provided at about 0.5%. In some embodiments, the *Ledum palustre* extract is provided at about 1.0%.

*Leuconostoc*/Radish Root Ferment Filtrate

Compositions as described herein, in some embodiments, comprise *Leuconostoc*/radish root ferment filtrate. In some embodiments, the *Leuconostoc*/radish root ferment filtrate is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the *Leuconostoc*/radish root ferment filtrate is provided in a range of about 0.25% to about 10%, about 0.5% to about 8%, about 0.75% to about 6%, or about 1% to about 4% by weight. In some embodiments, the *Leuconostoc*/radish root ferment filtrate is provided in a range of about 0.001% to about 6%, about 0.002% to about 4%, about 0.01% to about 3%, about 0.02% to about 2% by weight, or about 0.1% to about 2.5%. In some embodiments, the *Leuconostoc*/radish root ferment filtrate is provided at about 0.25%. In some embodiments, the *Leuconostoc*/radish root ferment filtrate is provided at about 0.5%. In some embodiments, the *Leuconostoc*/radish root ferment filtrate is provided at about 1.0%.

Lactoferrin

Compositions as described herein, in some embodiments, comprise a transferrin. In some embodiments, the transferrin is a lactoferrin. In some embodiments, lactoferrin is encapsulated in a liposome. Lactoferrin has wound healing attributes, promotes proliferation of fibroblasts and increases HA secretion. See Saito S, Takayama Y, Mizumachi K, Suzuki C. Lactoferrin promotes hyaluronan synthesis in human dermal fibroblasts. *Biotechnology letters.* 2011; 33(1):33-39; Takayama Y. Effects of Lactoferrin on Skin Wound Healing. In: *Lactoferrin and its Role in Wound Healing.* 2012:87-100.

In some instances, the lactoferrin has antimicrobial activity. In some instances, the lactoferrin has antimicrobial activity against bacteria, fungi, yeasts, viruses, parasites, or combinations thereof. Lactoferrin, in some instances, comprises antibiofilm activity. In some instances, lactoferrin interacts with the bacterial surface and destabilizes the microbial membrane. In some instances, lactoferrin chelates iron to disrupt the microbial membrane.

In some embodiments, lactoferrin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the lactoferrin is provided in a range of about 0.005% to about 0.1%, about 0.25% to about 10%, about 0.5% to about 8%, about 0.75% to about 6%, or about 1% to about 4% by weight. In some embodiments, the lactoferrin is provided in a range of about 0.001% to about 6%, about 0.002% to about 4%, about 0.01% to about 2.5%, or about 0.02% to about 2% by weight. In some embodiments, the lactoferrin is provided at about 0.025%. In some embodiments, the lactoferrin is provided at about 0.05%. In some embodiments, the lactoferrin is provided at about 0.10%. In some embodiments, the lactoferrin is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the lactoferrin is provided in a range of about 5 to about 1000, about 10 to about 900, about 30 to about 800, about 50 to about 700, about 60 to about 600, or about 100 to about 500 microgram per milliliter (ug/mL).

Dill Extract

Compositions as described herein, in some embodiments, comprise dill extract. The dill extract, in some embodiments, stimulates LOXL reinduction and elastin formation. In some embodiments, the dill extract is *Anethum graveolens* extract. In some embodiments, the dill extract is *Peucedanum graveolens* extract.

In some embodiments, the dill extract is provided at least or about 0.01%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the dill extract is provided in a range of about 0.25% to about 10%, about 0.025% to about 4%, about 0.5% to about 8%, about 0.75% to about 6%, or about 1% to about 4% by weight. In some embodiments, the dill extract is provided at about 1.0% by weight.

Hydroxymethoxyphenyl Decanone

Compositions as described herein, in some embodiments, comprise hydroxymethoxyphenyl decanone. In some embodiments, the hydroxymethoxyphenyl decanone is a potent intrinsic hyaluronic acid booster, antioxidant, anti-irritant, or a combination thereof.

In some embodiments, hydroxymethoxyphenyl decanone is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the hydroxymethoxyphenyl decanone is provided in a range of about 0.25% to about 10%, about 0.1% to about 2.5%, about 0.5% to about 8%, about 0.75% to about 6%, or about 1% to about 4% by weight. In some embodiments, the hydroxymethoxyphenyl decanone is provided in a range of about 0.001% to about 6%, about 0.002% to about 4%, about 0.01% to about 3%, or about 0.02% to about 2% by weight.

*Tremella Fuciformis*

Compositions as described herein, in some embodiments, comprise *Tremella fuciformis* extract. In some embodiments, the *Tremella fuciformis* extract is derived from an edible mushroom. In some embodiments, *Tremella fuciformis* extract provides moisture and antioxidant properties.

In some embodiments, *Tremella fuciformis* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the *Tremella fuciformis* extract is provided in a range of about 0.25% to about 10%, about 0.1% to about 2.5%, about 0.5% to about 8%, about 0.75% to about 6%, or about 1% to about 4% by weight. In some embodiments, the *Tremella fuciformis* extract is provided in a range of about 0.001% to about 6%, about 0.002% to about 4%, about 0.01% to about 3%, or about 0.02% to about 2% by weight.

Sodium Hyaluronate Crosspolymer

Compositions as described herein, in some embodiments, comprise sodium hyaluronate crosspolymer. Sodium hyaluronate crosspolymer is a high molecular weight synthetic hyaluronic acid with high water-binding capacity and moisturizing abilities.

In some embodiments, the sodium hyaluronate crosspolymer is provided at least or about 0.0001%, 0.0005%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4.0% by weight (wt. %). In some embodiments, the sodium hyaluronate crosspolymer is provided at about 0.5% by weight. In some embodiments, the sodium hyaluronate crosspolymer is provided in a range of about 0.0001% to about 4.0%, about 0.001% to about 4.0%, about 0.01% to about 3.0%, about 0.1% to about 2.5%, or about 0.50% to about 1.5% by weight.

Phytoene and Phytofluene

Compositions as described herein, in some embodiments, comprise phytoene, phytofluene, or combinations thereof. Phytoene and phytofluene are colorless carotenoids derived from saltwater microalgae that modulate Prostaglandin E-2 (PGE-2).

In some embodiments, the phytoene, phytofluene, or combinations thereof is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the phytoene, phytofluene, or combinations thereof is provided in a range of about 0.25% to about 10%, about 0.1% to about 2.5%, about 0.5% to about 8%, about 0.75% to about 6%, or about 1% to about 4% by weight. In some embodiments, the phytoene, phytofluene, or combinations thereof is provided in a range of about 0.001% to about 6%, about 0.002% to about 4%, about 0.01% to about 3%, or about 0.02% to about 2% by weight.

Xylitol

Compositions as described herein, in some embodiments, comprise xylitylglucoside, anhydroxylitol, xylitol, or combinations thereof. Xylitol is a sugar alcohol and comprises anti-biofilm and anti-inflammatory effects. In some embodiments, xylitol and lactoferrin in combination comprise anti-biofilm effects. In some embodiments, xylitol and lactoferrin act synergistically. For example, lactoferrin destabilizes the bacterial membrane and allows xylitol to cross the bacterial membrane to inhibit biofilm development and growth.

In some embodiments, the xylitylglucoside, anhydroxylitol, xylitol, or combinations thereof is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the xylitylglucoside, anhydroxylitol, xylitol, or combinations thereof is provided in a range of about 0.25% to about 10%, about 0.1% to about 2.5%, about 0.5% to about 8%, about 0.75% to about 6%, or about 1% to about 4% by weight. In some embodiments, the xylitylglucoside, anhydroxylitol, xylitol, or combinations thereof is provided in a range of about 0.001% to about 6%, about 0.002% to about 4%, about 0.01% to about 3%, or about 0.02% to about 2% by weight.

Sorbitan Isostearate

Compositions as described herein, in some embodiments, comprise sorbitan isostearate. In some embodiments, the sorbitan isostearate is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the sorbitan isostearate is provided in a range of about 0.25% to about 10%, about 0.1% to about 2.5%, about 0.5% to about 8%, about 0.75% to about 6%, or about 1% to about 4% by weight. In some embodiments, the sorbitan isostearate is provided in a range of about 0.001% to about 6%, about 0.002% to about 4%, about 0.01% to about 3%, or about 0.02% to about 2% by weight. In some embodiments, the sorbitan isostearate is provided at about 0.10% by weight.

Glucose

In some embodiments, compositions as described herein comprise glucose. In some embodiments, the glucose is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the glucose is provided in a range of about 0.25% to about 10%, about 0.1% to about 2.5%, about 0.5% to about 8%, about 0.75% to about 6%, or about 1% to about 4% by weight. In some embodiments, the glucose is provided in a range of about 0.001% to about 6%, about 0.002% to about 4%, about 0.01% to about 3%, or about 0.02% to about 2% by weight. In some embodiments, the glucose is provided at about 0.01% by weight.

Compositions as described herein, in some embodiments, comprise seed oil. In some embodiments, the seed oil is *Helianthus annuus* (sunflower) seed oil. In some embodiments, the seed oil is provided at least or about 0.001%, 0.003%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the seed oil is provided in a range of about 0.25% to about 10%, about 0.1% to about 2.5%, about 0.5% to about 8%, about 0.75% to about 6%, or about 1% to about 4% by weight. In some embodiments, the seed oil is provided in a range of about 0.001% to about 6%, about 0.002% to about 4%, about 0.01% to about 3%, or about 0.02% to about 2% by weight. In some embodiments, the seed oil is provided at about 0.003% by weight.

Other Components

Other components can include anti-inflammatory agents, antioxidants, and solubility enhancers. Exemplary anti-irritation agents include, but are not limited to, panthenyl triacetate and naringenin. Panthenyl triacetate and naringenin are natural plant extracts that reduce redness and water loss through the skin. Typical amounts for anti-irritation agents when employed in compositions are from 1% by weight to 4% by weight (wt. %).

Exemplary antioxidant agents include, but are not limited to, *Dunaliella salina* extract and squalane. *Dunaliella salina* extract includes components such as beta carotenes. It can exhibit an antioxidant effect. Typical amounts for anti-inflammatory agents when employed in compositions are from 0.1% by weight to 2.5% by weight (wt. %). In some embodiments, the *Dunaliella salina* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the *Dunaliella salina* extract is provided in a range of about 0.001% to about 4.0%, about 0.01% to about 3.0%, about 0.1% to about 2.5%, or about 0.50% to about 1.5%. In some embodiments, the squalane is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the squalane is provided in a range of about 0.001% to about 4.0%, about 0.01% to about 3.0%, about 0.1% to about 2.5%, or about 0.50% to about 1.5%. In some embodiments, the *Dunaliella salina* extract and the squalane is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the *Dunaliella salina* and the squalane extract is provided in a range of about 0.001% to about 4.0%, about 0.01% to about 3.0%, about 0.1% to about 2.5%, or about 0.50% to about 1.5%.

In some embodiments, the composition comprises a siloxane polymer. In some embodiments, the siloxane polymer is caprylyl methicone. In some embodiments, caprylyl methicone is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4.0% by weight (wt. %). In some embodiments, the caprylyl methicone is provided at about 0.5% by weight. In some embodiments, the caprylyl methicone is provided in a range of about 0.001% to about 4.0%, about 0.01% to about 3.0%, about 0.1% to about 2.5%, or about 0.50% to about 1.5% by weight. In some embodiments, the caprylyl methicone is provided at about 0.25% by weight. In some embodiments, the caprylyl methicone is provided at about 1% by weight.

Bentonite clays can be employed in conjunction with the peptides to provide impart penetration and adsorption properties to the compositions, and can aid in stabilizing emulsions. Other clays, such as hectorite and magnesium aluminum silicate can also be employed. Bentonite or other clays can be modified to yield an organic modified clay compound. Salts (e.g., quaternary ammonium salts) of fatty acids (e.g., hydrogenated fatty acids) can be reacted with hectorite or other clays. As provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by $\Delta n$, where n indicates the lower numbered carbon of each pair of double-bonded carbon atoms. A shorthand notation specifying total #carbons: #double bonds, $\Delta_{double\ bond\ positions}$ can be employed. For example, $20:4\Delta_{5, 8,11,14}$ refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-$\Delta$9-octadecenoate) is a monounsaturated fatty acid, linolenate (all-cis-$\Delta$9,12,15-octadecatrienoate) is a polyunsaturated fatty acid. Fatty acids suitable for use can comprise from 5 to 30 carbon atoms, e.g., 5, 6, 7, 8, 9, 10, 11, 12, 13, 14, 15, 16, 17, 18, 19, 20, 21, 22, 23, 24, 25, 26, 27, 28, 29, or 30 carbon atoms. The fatty acid can be fully saturated, or can include as many double bonds as are feasible for the chain length. Fatty acids suitable for functionalizing hectorite or other clays include palmitic acid and stearic acid. Dialkyl quaternary cationic modifiers include dipalmoyldimonium chloride and distearyldimonium chloride. Amido-amine quaternary cationic modifiers include palmitamidopropyltrimonium chloride cetearyl alcohol and palmitamidopropyltrimonium chloride.

In some embodiments, the peptides can be in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for compositions include, without limitation, monoglycerides, diglycerides, sulfatides, lysolecithin, phospholipids, saponin, bile acids, and the like. In some embodiments, compositions described herein comprise, phosphatidylserine, phospholipids, tocopherol, ascorbyl palmitate, or combinations thereof. In some embodiments, phosphatidylserine, phospholipids, tocopherol, ascorbyl palmitate, or combinations thereof is provided at 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the phosphatidylserine, phospholipids, tocopherol, ascorbyl palmitate, or combinations thereof is provided in a range of about 0.25% to about 10%, about 0.5% to about 8%, about 0.75% to about 6%, or about 1% to about 4% by weight. In some embodiments, the phosphatidylserine, phospholipids, tocopherol, ascorbyl palmitate, or combinations thereof is provided in a range of about 0.001% to about 6%, about 0.002% to about 4%, about 0.01% to about 3%, or about 0.02% to about 5% by weight. In some embodiments, the additive is betaine. Betaine, in some embodiments, is provided in a range of about 0.001% to about 6%, about 0.002% to about 4%, about 0.01% to about 3%, or about 0.02% to about 5% by weight. In some embodiments, the compositions as described herein comprise caprylyl glycol. In some embodiments, the caprylyl glycol provided in a range of about 0.001% to about 6%, about 0.002% to about 4%, about 0.01% to about 3%, or about 0.02% to about 5% by weight. In some embodiments, the compositions as described herein comprise caprylhydroxamic acid. In some embodiments, the caprylhydroxamic acid provided in a range of about 0.001% to about 6%, about 0.002% to about 4%, about 0.01% to about 3%, or about 0.02% to about 5% by weight. The presence of such additional components can influence the physical state, solubility, stability, rate of release, rate of clearance, and penetration of active ingredients.

The compositions for topical administration or application comprise the peptide compositions as described herein and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered or applied topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the peptides into the skin. An alternative to increasing molecular weight (as with silicone gums) or adding filler (as with silicone compounds) is to partially crosslink siloxane polymers and disperse this material in an appropriate silicone carrier fluid. The resulting dimethicone crosspolymers (also known as silicone elastomers in the personal care industry) differ from basic polydimethylsiloxane (PDMS) because of the cross-linking between the linear polymers. These materials can be employed in peptide compositions, and also offer benefits in scar treatment, periwound protection and enzyme delivery. In skin care applications, the aesthetics of silicone elastomers (including those with functional groups) and their ability to absorb various oils (e.g., with a dimethicone/vinyl dimethicone crosspolymer such as Dow Corning® 9506 Elastomer Powder) are two of the elastomer's desirable properties. Silicone elastomers have a skin feel different from any of the silicone fluids, described as "smooth," "velvety," and "powdery." It can be modified by controlling the amount of liquid phase in the formula, and therefore the degree of swelling. Due to their film-forming properties, dimethicone crosspolymers can be used as delivery systems for active ingredients such as the peptides described herein, or other composition components such as oil-soluble vitamins and sunscreens. Sunscreens such as octyl methoxycinnamate can be more efficiently delivered from a composition containing a silicone elastomer, producing a higher sun protection factor (SPF). Silicone elastomer blends can be used to enhance SPF in oil-in-water compositions containing organic sunscreens. For example, in testing conducted regarding SPF, the addition of 4% silicone elastomer blend to a sun care composition containing organic sunscreens increased the SPF from 5.7 to 18. This property of the silicone elastomer allows the effectiveness of sunscreen agents in a composition to be maximized while reducing the amount needed to achieve a desired SPF. As a result, composition costs can be reduced along with potential irritation caused by sunscreen actives. Accordingly, a higher SPF can be achieved with the same amount of UV absorber, resulting in enhanced performance with no added composition cost. Silicone elastomers can be produced from linear silicone polymers by a variety of crosslinking reactions, e.g., by a hydrosilylation reaction in which a vinyl group reacts with a silicon hydride. The general process involves linear silicone polymers with reactive sites along the polymer chain reacting with a cross-linker. The dimethicone crosspolymer can be produced either as a gel made of a suspension of elastomer particles swollen in a carrier fluid (e.g., a mixture of high molecular weight silicone elastomer in cyclopentasiloxane such as Dow Corning® 9040 Silicone Elastomer Blend), or as a spray-dried powder (a dimethicone/vinyl dimethicone crosspolymer such as Dow Corning® 9506 Elastomer Powder). The gel form having desirable attributes is cyclomethicone, but low viscosity dimethicones and organic fluids can also be used. Examples of dimethicone crosspolymers in the suspension or gel form are high molecular weight silicone elastomer (12%) in decamethylcyclopentasiloxane (e.g., Dow Corning® ST-Elastomer 10) and a mixture of high molecular weight silicone elastomer in cyclopentasiloxane (e.g., Dow Corning® 9040 Silicone Elastomer Blend), which typically have an elastomer content ranging from 10 to 20% by weight.

The pharmaceutical excipients used in the topical preparations of the peptide compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic liposomal composition include water; ethyl alcohol; isopropyl alcohol; mixtures of water and ethyl and/or isopropyl alcohols; glycerin; ethylene, propylene or butylene glycols; DMSO; pentylene glycol; and mixtures thereof. In some embodiments, glycerin is provided at least or about 1%, 2%, 3%, 4%, 5%, 6%, 7%, 8%, 9%, 10%, 11%, 12%, or more than 12% by weight (wt. %). In some embodiments, glycerin is provided at least or about 7%. In some embodiments, glycerin is provided in a range of about 1% to about 12%, about 2% to about 11%, or about 3% to about 10% by weight. In some embodiments, butylene glycol is provided at least or about 0.0025%, 0.005%, 0.075%, 0.01%, 0.025%, 0.05%, 0.75%, 1%, 2%, 3% 4%, 5%, 6%, 7% 8%, 9% 10%, 11%, 12%, or more than 12% by weight. In some embodiments, butylene glycol is provided in a range of about 0.01% to about 10%, about 0.025% to about 5%, or about 0.05% to about 1.25% by weight. In some embodiments, pentylene glycol is provided at least or about 0.0025%, 0.005%, 0.075%, 0.01%, 0.025%, 0.05%, 0.75%, 1%, 2%, 3%, 4%, 5%, 6%, 7% 8%, 9%, 10%, 11%, 12%, or more than 12% by weight. In some embodiments, pentylene glycol is provided in a range of about 0.01% to about 10%, about 0.025% to about 5%, or about 0.05% to about 1.25% by weight. Suitable solvents for hydrophobic compositions include mineral oils, vegetable oils, and silicone oils. If desired, the peptide compositions as described herein may be dissolved or dispersed in a hydrophobic oil phase, and the oil phase may then be emulsified in an aqueous phase comprising water, alone or in combination with lower alcohols, glycerin, and/or glycols. In some embodiments, an anhydrous composition is applied as the presence of water can result in stinging upon administration to skin tissues subject to laser treatment, chemical peel, dermabrasion, or the like. Anhydrous compositions may also act to prevent the development of water-based irritant contact dermatitis in damaged or sensitive skin, which may produce rashes and skin irritation that may retard wound healing and improvement in skin quality. Tsai, T. F., Maibach, H. I. How irritant is water? An overview. Contact Dermatitis 41(6) (1999): 311-314 (describing contact dermatitis caused by water as an irritant). However, in certain embodiments it may be acceptable to provide water based compositions, or to permit a limited amount of water to be present. For example, water may be present, but at amounts below the threshold at which a stinging sensation when applied to damaged skin may result. Osmotic shock or osmotic stress is a sudden change in the solute concentration around a cell, causing a rapid change in the movement of water across its cell membrane. Under conditions of high concentrations of either salts, substrates or any solute in the supernatant, water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis. Certain of the compositions as described herein can be advantageously employed where it is desirable to minimize osmotic shock.

Compositions as described herein may comprise varying amounts of solvent. In some embodiments, the solvent is water. In some embodiments, the solvent is at least or about 10%, 15%, 20%, 25%, 30%, 35%, 40%, 45%, 50%, 55%, 60%, 65%, 70%, 75%, 80%, 85%, 90%, 95%, or more than 95% by weight (wt. %). In some embodiments, the solvent is in a range of about 10% to about 95%, about 20% to about 90%, about 30% to about 85%, about 40% to about 80%, or about 50% to about 75% by weight.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carrageenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

The viscosity of the compositions as described herein, in some embodiments, are in a range of about 8,000 centipoise (cps) to about 30,000 cps. In some embodiments, the viscosity is at least or about 4,000; 5,000; 6,000; 7,000; 8,000; 9,000; 10,000; 11,000; 12,000; 13,000; 14,000; 15,000; 16,000; 17,000; 18,000; 19,000; 20,000; 21,000; 22,000; 23,000; 24,000; 25,000; 26,000; 27,000; 28,000;29,000; 30,000; 31,000; 32,000; 33,000; 34,000, 35,000; 36,000; 37,000; 38,000; 39,000; 40,000; or more than 40,000 cps. In some embodiments, the composition comprises a viscosity in a range of about 4,000 to about 40,000, about 6,000 to about 38,000, about 8,000 to about 36,000, about 10,000 to about 34,000 cps, about 12,000 to about 32,000 cps, or about 14,000 to about 30,000 cps.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids. In some embodiments, the emollient is caprylic/capric triglyceride.

In some embodiments, the emollient is provided at least or about 0.0025%, 0.005%, 0.075%, 0.01%, 0.025%, 0.05%, 0.75%, 1%, 2%, 3%, 4%, 5%, 6%, 7%, 8%, 9%, 10%, 11%, 12%, or more than 12% by weight. In some embodiments, the emollient is provided in a range of about 0.01% to about 10%, about 0.01% to about 2.5%, about 0.025% to about 5%, or about 0.05% to about 1.25% by weight. In some embodiments, the caprylic/capric triglyceride is provided at least or about 0.0025%, 0.005%, 0.075%, 0.01%, 0.025%, 0.05%, 0.75%, 1%, 2%, 3%, 4%, 5%, 6%, 7%, 8%, 9%, 10%, 11%, 12%, or more than 12% by weight. In some embodiments, the caprylic/capric triglyceride is provided in a range of about 0.01% to about 10%, about 0.01% to about 2.5%, about 0.025% to about 5%, or about 0.05% to about 1.25% by weight.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the compositions include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the compositions. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1,3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in compositions include anionic, cationic, nonionic, and zwitterionic surfactants. Preferred ionic emulsifiers include phospholipids, such as lecithin and derivatives.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in compositions include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the composition. It is generally observed that the anhydrous compositions of the embodiments exhibit satisfactory stability, such that a preservative can be omitted from the composition.

Suitable chelating agents for use in compositions include ethylene diamine tetraacetic acid, alkali metal salts thereof alkaline earth metal salts thereof, ammonium salts thereof, and tetraalkyl ammonium salts thereof. In some embodiments, the chelating agent is disodium ethylenediaminetetraacetic acid (EDTA). In some embodiments, the disodium EDTA is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the disodium EDTA is provided in a range of about 0.25% to about 10%, about 0.1% to about 2.5%, about 0.5% to about 8%, about 0.75% to about 6%, or about 1% to about 4% by weight. In some embodiments, the disodium EDTA is provided in a range of about 0.001% to about 6%, about 0.002% to about 4%, about 0.01% to about 3%, or about 0.02% to about 2% by weight.

The carrier preferably has a pH of between about 4.0 and 10.0, more preferably between about 4.8 and about 7.8, more preferably between about 5.0 to about 6.5. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The peptide compositions of the embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the composition, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

In certain embodiments, the addition of emollients, emulsion stabilizers, moisturizers, excipients, and other compounds may be modified to enhance the sensory properties of the topical compositions, including but not limited to: skin feel (silkiness, lightness, creaminess, etc.), absorbency (required time at which product loses wet feel and is no longer perceived on skin), consistency, firmness, spreadability (e.g. viscosity, flow onset, shear rates), stickiness, integrity of shape, glossiness, hydrophilicity or hydrophobicity, and others. Preferably, compositions will have high spreadability and low viscosity properties. Compositions with such properties have been demonstrated to have an enhanced "silky" or "light" skin feel rating (see e.g. Bekker, M. Webber, G., Louw, N. Relating rheological measurements to primary and secondary skin feeling when mineral-based and Fischer-Tropsch wax-based cosmetic emulsions and jellies are applied to the skin, International Journal of Cosmetic Science 2013, 35(4), pp. 354-61).

In some embodiments, compositions comprise phenoxyethanol, ethylhexylglycerin, or combinations thereof. In some embodiments, phenoxyethanol is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, phenoxyethanol is provided in a range of about 0.25% to about 10%, about 0.5% to about 8%, about 0.75% to about 6%, or about 1% to about 4% by weight. In some embodiments, ethylhexylglycerin is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, ethylhexylglycerin is provided in a range of about 0.25% to about 10%, about 0.5% to about 8%, about 0.75% to about 6%, or about 1% to about 4% by weight. In some embodiments, phenoxyethanol and ethylhexylglycerin are provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, phenoxyethanol and ethylhexylglycerin are provided in a range of about 0.25% to about 10%, about 0.1% to about 4%, about 0.5% to about 8%, about 0.75% to about 6%, or about 1% to about 4% by weight.

In some embodiments, compositions comprise polyacrylate-13, polyisobutene, polysorbate 20, or combinations thereof. In some embodiments, polyacrylate-13 is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, polyacrylate-13 is provided in a range of about 0.25% to about 10%, about 0.5% to about 8%, about 0.75% to about 6%, or about 1% to about 4% by weight. In some embodiments, polyisobutene is provided at least or about 0.05%, 0.10%, 0.25%, 0.50%, 0.75%, 1.0%, 1.5%, 2.0%, 2.5%, 3.0%, 3.5% 4.0%, 4.5% 5.0%, 5.5% 6.0%, 6.5%, 7.0%, 8%, 9%, 10%, or more than 10% by weight (wt. %). In some embodiments, polyisobutene is provided in a range of about 0.25% to about 10%, about 0.5% to about 8%, about 0.75% to about 6%, or about 1% to about 4% by weight. In some embodiments, polyacrylate-13 is provided in a range of about 0.25% to about 10%, about 0.5% to about 8%, about 0.75% to about 6%, or about 1% to about 4% by weight. In some embodiments, polysorbate 20 is provided at least or about 0.05%, 0.10%, 0.25%, 0.50%, 0.75%, 1.0%, 1.5%, 2.0%, 2.5%, 3.0%, 3.5%4, 4.0%, 4.5%, 5.0%, 5.5%, 6.0%, 6.5%, 7.0%, 8%, 9%, 10%, or more than 10% by weight (wt. %). In some embodiments, polysorbate 20 is provided in a range of about 0.25% to about 10%, about 0.5% to about 8%, about 0.75% to about 6%, or about 1% to about 4% by weight. In some embodiments, polyacrylate-13, polyisobutene, and polysorbate 20 are provided at least or about 0.05%, 0.10%, 0.25%, 0.50%, 0.75%, 1.0%, 1.5%, 2.0%, 2.5%, 3.0%, 3.5%4, 4.0%, 4.5%, 5.0%, 5.5%, 6.0%, 6.5%, 7.0%, 8%, 9%, 10%, or more than 10% by weight (wt. %). In some embodiments, polyacrylate-13, polyisobutene, and polysorbate 20 are provided in a range of about 0.25% to about 10%, about 0.1% to about 4%, about 0.5% to about 8%, about 0.75% to about 6%, or about 1% to about 4% by weight (wt. %).

In some embodiments, compositions as described herein comprise potassium sorbate. In some embodiments, the potassium sorbate is provided at least or about 0.001%, 0.00175%, 0.0025%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the potassium sorbate is provided in a range of about 0.001% to about 6%, about 0.002% to about 4%, about 0.01% to about 3%, or about 0.02% to about 2% by weight.

In some embodiments, the liposomes comprise propanediol, lecithin, or a combination thereof. In some embodiments, the propanediol is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol is provided in a range of about 0.001% to about 6%, about 0.002% to about 4%, about 0.01% to about 3%, or about 0.02% to about 2% by weight. In some embodiments, the lecithin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the lecithin is provided in a range of about 0.001% to about 6%, about 0.002% to about 4%, about 0.01% to about 3%, or about 0.02% to about 2% by weight. In some embodiments, the liposomes comprise propanediol and lecithin. In some embodiments, the propanediol and lecithin are provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5% 4.0%, 4.5% 5.0%, 5.5%, 6.0%, 6.5%, 7.0%, 8%, 9%, 10%, or more than 10% by weight (wt. %). In some embodiments, the propanediol and lecithin are provided in a range of about 0.001% to about 6%, about 0.002% to about 4%, about 0.01% to about 3%, or about 0.02% to about 2% by weight. In some embodiments, the propanediol and lecithin are provided at about 0.90% by weight.

The topical composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting composition contains micelles, i.e., spherical oil droplets Penetration Enhancers Fatty acids and alcohols can be employed to enhance penetration of the peptides, and to provide a silky feel to compositions, e.g., methanoic acid, ethanoic acid, propanoic acid, butanoic acid, isobutyric acid, pentanoic acid, hexanoic acid, heptanoic acid, octanoic acid, nonanoic acid, decanoic acid, myristoleic acid, isovaleric acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, medium chain fatty acids, e.g., $C_6$-12 fatty acids, or the like. Typical amounts when employed in compositions are from 1% by weight to 4% by weight.

Antimicrobial Efficacy

Described herein, in some embodiments, are chemically and physically stable compositions at physiological pH. In some embodiments, the compositions are sterile and safe for human administration or application. In some embodiments, the compositions comply with or pass the required antimicrobial efficacy tests such as the Antimicrobial Effectiveness Test. In some embodiments, the compositions result in complete or substantially complete eradication of bacteria, yeast, mold, or combinations thereof.

Compositions Comprising Hyaluronic Acid

Described herein, in some embodiments, are compositions comprising hyaluronic acid that are used in conjunction with compositions described herein for improving bruising. In some embodiments, the compositions comprising hyaluronic acid are administered or applied prior to, concurrently, or after administration or application with compositions described herein for improving bruising. In some embodiments, the compositions comprising hyaluronic acid is in a form of a filler.

Compositions described herein, in some embodiments, comprise hyaluronic acid. In some embodiments, the hyaluronic acid (HA) is a gel. In some embodiments, the hyaluronic acid is avian HA, bovine HA, non-animal stabilized HA, or combinations thereof.

In some embodiments, the composition is a cross-linked biocompatible polysaccharide (e.g, hyaluronic acid) gel composition. In some embodiments, the composition is formed by forming an aqueous solution of a water soluble, cross-linkable polysaccharide; initiating a cross-linking of said polysaccharide in the presence of a polyfunctional cross-linking agent; sterically hindering the cross-linking reaction from being terminating before gelation occurs, an activated polysaccharide thereby being obtained; and reintroducing sterically unhindered conditions for said activated polysaccharide so as to continue the cross-linking thereof up to a viscoleastic gel.

In some embodiments, the composition is a cross-linked biocompatible hyaluronic acid gel composition comprising various degrees of cross-linking. In some embodiments, the degree of cross-linking is at least or about 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, 11%, 12%, 13%, 14%, 15%, or more than 15%. In some embodiments, the degree of cross-linking is in a range of about 1% to about 20%, about 1% to about 15%, about 1% to about 10%, about 5% to about 20%, about 5% to about 15%, or about 5% to about 10%.

In some embodiments, the composition comprises a high elastic modulus or G'. In some embodiments, the composition comprises a G' of at least or about 5, 10, 20, 25, 50, 75, 100, 150, 200, 250, 275, 300, 325, 350, 375, 400, 425, 450, 475, 500, 525, 550, 575, 600, 625, 650, 675, 700, 725, 750, 775, 800, or more than 800 pascals. In some embodiments, the composition comprises a G' in a range of about 5 to about 800, about 5 to about 700, about 5 to about 600, about 5 to about 500, about 5 to about 400, about 5 to about 300, about 5 to about 200, about 5 to about 100, about 5 to about 50, about 25 to about 800, about 25 to about 700, about 25 to about 600, about 25 to about 500, about 25 to about 400, about 25 to about 300, about 25 to about 200, about 25 to about 100, about 25 to about 50, about 50 to about 800, about 50 to about 700, about 50 to about 600, about 50 to about 500, about 50 to about 400, about 50 to about 300, about 50 to about 200, about 50 to about 100, or about 50 to about 75 pascals.

In some embodiments, the hyaluronic acid is generated by a Streptococcus species of bacteria. In some embodiments, the hyaluronic acid is stabilized, e.g., non-animal stabilized. In some embodiments, the hyaluronic acid is chemically crosslinked with BDDE (1,4 butanediol diglycidyl ether), stabilized, and suspended in phosphate buffered saline at a pH of 7 and a concentration of 20 mg/mL. In some embodiments, the hyaluronic acid is free of animal protein. For example, in some embodiments, the hyaluronic acid is a gel generated by a Streptococcus species of bacteria, chemically cross-linked with BDDE, stabilized, and suspended in saline at pH 7 (e.g., as in RESTYLANE® dermal filler, RESTYLANE TOUCH™ dermal filler, RESTYLANE FINE LINES™ dermal filler, RESTYLANE VITAL™ dermal filler, and RESTYLANE LIPP™ dermal filler). In some embodiments, the hyaluronic acid is provided at a concentration of 20 mg/mL, phosphate buffered at pH 7, and/or free of animal protein. In some embodiments, the hyaluronic acid is one that is suitable for injection into a dermal location where it acts to stimulate collagen synthesis.

In some embodiments, the hyaluronic acid is in the form of gel particles. In some embodiments, the hyaluronic acid is in the form of gel particles having sizes in the range of about 940 microns to about 1090 microns. In some embodiments, the largest fraction of gel particles size is between 940 microns and 1090 microns. In some embodiments, the hyaluronic acid gel particles have a particle size that is less than 1200 microns. In some embodiments, the hyaluronic acid gel particles have a particle size that is about 400 microns. In some embodiments, the hyaluronic acid gel particles have a particle size that is less than 400 microns. In some embodiments, the hyaluronic acid gel particles have a particle size that is more than 400 microns. In some embodiments, the hyaluronic acid gel particles have a particle size that is in the range of about 400 to about 1200 microns.

The concentration of hyaluronic acid gel particles in the dermal filler may vary over a broad range, e.g., about 500-200,000 particles per mL, such as about 500-5000 particles per ml, about 5,000-50,000 particles per ml, about 50,000-150,000 particles per ml, or about 150,000-200,000 particles per ml. For example, in some embodiments, the dermal filler comprises about 200,000 hyaluronic acid gel particles per mL. In some embodiments, the dermal filler comprises about 100,000 hyaluronic acid gel particles per mL. In some embodiments, the dermal filler comprises about 10,000 hyaluronic acid gel particles per mL. In some embodiments, the dermal filler comprises about 1,000 hyaluronic acid gel particles per mL.

Alternatively, or in combination, additional biologic, biodegradable fillers are used. Biologic, biodegradable fillers include materials derived from organism, human, and/or animal tissues and/or products. Examples of such fillers include the following: hyaluronic acid, (such as the following: avian HA, bovine HA, and non-animal stabilized HA ("NASHA", e.g., RESTYLANE® (injectable filler)), collagen (such as collagen I, collagen II, collagen III, cross-linked and/or noncross-linked, bovine, porcine, human, and autologous collagen). Additional examples of collagen based fillers include ZYPLAST® (collagen derived from bovine tissue), ZYDERM® I (collagen derived from bovine tissue), ZYDERM® II, (collagen derived from bovine tissue), EVOLENCE™ (porcine derived collagen), and FIBREL™ (porcine derived collagen). In some embodiments, the injectable filler is self-replicating, and can include living cells (such as collagen-producing cells or fibroblasts). In some embodiments, the injectable filler is a biostimulatory filler or tissue-inducing filler. Biostimulatory or tissue-inducing fillers stimulate cellular production of natural collagen and include, but are not limited to, RADIESSE™ (microspheres of at least calcium and phosphate ions), SCULPTRA® (poly-L-lactic acid (PLLA)), BEL-LAFTLL® (microspheres of PMMA), SOFREGEN SILK VOICE® (at least silk protein microparticles), and similar fillers.

Examples of injectable fillers include a substance selected from the following: collagen, fat, human or animal derived collagen, bovine collagen, type I collagen, type II collagen, type III collagen, 3.5% bovine dermal collagen cross-linked by glutaraldehyde to form a latticework, natural human collagen, autologous collagen, polymethylmethacrylate microspheres (optionally suspended in bovine collagen), suspension of collagen fibers prepared from the subject's tissue, human tissue collagen matrix derived from cadaveric dermis, polyacids, polyethers (e.g., carboxymethyl cellulose (CMC) and polyethylene oxide), acellular human cadaveric dermis that has been freeze-dried, micronized acellular human cadaveric dermis that has been freeze-dried, cultured autologous fibroblasts, hyaluronic acid, non-animal-stabilized hyaluronic acid derivative, microspheres of calcium hydroxyl appetite suspended in an aqueous gel carrier, dextran beads suspended in hylan gel of nonanimal origin (e.g., 40- to 60-µm in diameter), solubilized elastin peptides with bovine collagen, silicone, solubilized elastin peptides with bovine collagen, poly-L-lactic acid, Gore-Tex (PTFE), glycosylated collagen, PMMA, bone-forming calcium apatite, cultured human cells, expanded polytetrafluoroethylene (e-PTFE), SOFTFORM® of ePTFE, and some combination thereof. Further examples of injectable fillers include the following: AQUAMID® (comprising water and cross-linked polymers), ARTEFIL® (polymethylmethacrylate (PMMA) microspheres suspended in bovine collagen), LARESSE® Dermal Filler (synthetic, biocompatible polymers, non-HA gel comprising absorbable medical polymers), ARTECOLL® (polymethylmethacrylate (PMMA) microspheres suspended in bovine collagen), BELOTERO®, BIO-ALCAMID™ (synthetic reticulate polymer (poly-alkyl-imide), CAPTIQUE™ (non-animal hyaluronic acid), COSMODERM™ (human collagen skin filler), COMOPLAST™, CYMETRA®, autologen, DER-MALOGEN®, FASCIAN™ (fascia), fascia, fat, Hylaform™ (avian hyaluronic acid), JUVEDERM® (bio-synthesized, non-animal hyaluronic acid), RADIESSE™ (microspheres of at least calcium and phosphate ions), SCULPTRA® (poly-L-lactic acid (PLLA)), collagen, hyaluronic acid, RESTYLANE®, PERLANE®, ZYDERM®, ZYPLAST® (collagen derived from bovine tissue), DERMALIVE®, (hyaluronic acid and acrylic hydrogel particles), DERMADEEP® (hyaluronic acid and acrylic hydrogel particles), HYDRAFILL®, ISOLAGEN® (cultured autologous human fibroblasts), LARESSE® (carboxymethylcellulose (CMC) and polyethylene oxide (PEO) filler), PURAGEN™ (filler comprising double cross-linked hyaluron molecules), REVIDERM® INTRA (filler comprising flexible dextran micro-beads suspended in super-coiled, stabilized hyaluronic acid), SCULPTRA™ (Formerly NEW-FILL™, filler from poly-L-lactic acid), Teosyal, SUR-GIDERM® (hyaluronic acid filler involving 3D hyaluronic acid matrix technology), OUTLINE®, ANIKA®, Cosmetic tissue augmentation (CTA, from Anika), and combinations thereof.

Methods of Use

Described herein are compositions and methods for improving bruising. Bruising can be caused by a variety of sources. In some embodiments, bruising is a result of a cosmetic procedure. In some embodiments, the compositions and methods described herein improve bruising prior to or after a cosmetic procedure. In some embodiments, the cosmetic procedure comprises injection of a filler. In some embodiments, the cosmetic procedure comprises injection of a hyaluronic acid filler.

Also described herein are compositions and methods for stimulation of increased collagen, elastin, fat, or hyaluronic acid. In some embodiments, the stimulation is adjunct to an injection of a soft tissue filler.

In some embodiments, the cosmetic procedure comprises injection of a filler. In some embodiments, the filler is a soft tissue filler product. For example, the soft tissue filler is an injectable dermal or subdermal filler. In some embodiments, the filler is a breast augmentation or reconstruction filler, a lip filler, or filler suitable for other soft tissue restoration or augmentation. In some embodiments, the filler is dermal filler. In some instances, the dermal filler is administered or applied through injection into or beneath the skin of a subject.

In some embodiments, the filler comprises hyaluronic acid. In some embodiments, the hyaluronic acid (HA) is a gel. In some embodiments, the hyaluronic acid is avian HA, bovine HA, non-animal stabilized HA, or combinations thereof.

In some embodiments, the hyaluronic acid is generated by a *Streptococcus* species of bacteria. In some embodiments, the hyaluronic acid is stabilized, e.g., non-animal stabilized. In some embodiments, the hyaluronic acid is chemically crosslinked with BDDE (1,4 butanediol diglycidyl ether), stabilized, and suspended in phosphate buffered saline at a pH of 7 and a concentration of 20 mg/mL. In some embodiments, the hyaluronic acid is free of animal protein. For example, in some embodiments, the hyaluronic acid is a gel generated by a *Streptococcus* species of bacteria, chemically cross-linked with BDDE, stabilized, and suspended in saline at pH 7 (e.g., as in RESTYLANE® dermal filler, RESTY-LANE TOUCH™ dermal filler, RESTYLANE FINE LINES™ dermal filler, RESTYLANE VITAL™ dermal filler, and RESTYLANE LIPP™ dermal filler). In some embodiments, the hyaluronic acid is provided at a concentration of 20 mg/mL, phosphate buffered at pH 7, and/or free of animal protein. In some embodiments, the hyaluronic acid is one that is suitable for injection into a dermal location where it acts to stimulate collagen synthesis.

In some embodiments, the filler (e.g., comprising hyaluronic acid) is administered or applied to various parts of the body. In some embodiments, the filler is administered or applied to the face. In some embodiments, the filler is administered or applied to smooth away facial wrinkles and folds. In some embodiments, the filler is administered or applied to the lips. In some embodiments, the filler is administered or applied to the lower lip, upper lip, or both.

In some embodiments, the filler is administered or applied to the lips to provide lip enhancements. In some embodiments, the filler is administered or applied around or near the mouth. In some embodiments, the filler is administered or applied around or near the mouth to smooth lines around or near the mouth. In some embodiments, the filler is administered or applied to the cheeks. In some embodiments, the filler is administered or applied to the chin. In some embodiments, the filler is administered or applied to the hands. In some embodiments, the filler is administered to the temple. In some embodiments, the filler is administered to the peri-ocular region. In some embodiments, the filler comprises hyaluronic acid.

In some embodiments, the filler (e.g., comprising hyaluronic acid) is administered or applied to a target area of the body. In some embodiments, the target area comprises a wrinkle, an oral commissure, a marionette line, mandibular hollow, raise jowls, a frowning mouth, a pouty lower lip, a lateral expression line, a mental crease, a chin dimpling, a zygomatic hollow, a nasolabial fold, a tear trough, or a brow lift.

In some embodiments, the filler (e.g., comprising hyaluronic acid) is administered or applied at various depth of injection. In some embodiments, the filler is administered or applied as a surface injection. In some embodiments, the filler is administered or applied as a mid-injection. In some embodiments, the filler is administered or applied as a deep-injection. In some embodiments, the filler is administered or applied as a mid-to-deep injection. In some embodiments, the filler is administered or applied mid-to-deep dermis (subcutaneous and/or supraperiosteal). In some embodiments, the filler is administered or applied at a depth to correct for moderate or severe wrinkles (e.g., perioral wrinkles) or folds (e.g., nasolabial folds), or for cheek augmentation, for the correction of age-related midface contour deficiencies, or combinations thereof. In some embodiments, the filler comprises hyaluronic acid.

In some embodiments, the amount of filler administered or applied is in the range of from about 0.01 cc to about 1 cc, for example 0.01-0.05, 0.05-0.1, 0.1-0.15, 0.15-0.2, 0.2-0.3, 0.3-0.4, 0.4-0.5, 0.5-0.6, 0.6-0.7, 0.7-0.8, 0.8-0.9, or 0.9-1 cc.

Methods and compositions as described herein may improve bruising following a cosmetic procedure. In some embodiments, methods and compositions improve bruising prior to a cosmetic procedure. In some instances, bruising is caused by red blood cells. Generally, red blood cells efficiently bind oxygen from the atmosphere, deliver it to the tissues, and help remove carbon dioxide. In some instances, red blood cells are involved in pathophysiologic problems with hemorrhage and extravasation of these cells into the tissue. Once outside the vascular system, red blood cells can quickly burst releasing free hemoglobin (Hb). That Hb may be prone to spontaneous oxidation and may be converted to higher oxidation states such as ferrylHb which have potent pro-inflammatory and pro-oxidant effects. See Jeney V, Eaton J W, Balla G, Balla J. Natural history of the bruise: formation, elimination, and biological effects of oxidized hemoglobin. *Oxidative medicine and cellular longevity.* 2013; 2013:703571. The heme that is released may be phagocytosed by macrophages. Following internalization by the macrophage, heme is cleaved into biliverdin, carbon monoxide, and iron. This mechanism can provide effective elimination of Hb, but it also assures iron recycling for new erythropoiesis (new red blood cell formation) under normal circumstances. See Jeney V, Eaton J W, Balla G, Balla J. Natural history of the bruise: formation, elimination, and biological effects of oxidized hemoglobin. *Oxidative medicine and cellular longevity.* 2013; 2013:703571. In some instances, leaving the byproducts of bleeding around for too long runs the risk of the pro-inflammatory effects. In some instances, these effects interfere with wound healing, promote pigmentation, or are unsightly. In some instances, delayed bruising results. See Sadeghpour M, Dover J S. Understanding Delayed Bruising After Hyaluronic Acid Injections: Why the Molecule and Not Just the Injection Matters—letters and communications. *Dermatol Surg.* 2019; 45(3):471-473. Compositions and methods as described herein, in some embodiments, improve bruising by removing by-products of red blood cell extravasation more efficiently. In some embodiments, compositions described herein result in improving function of macrophages.

Compositions as described herein comprising lactoferrin, phosphatidylserine, tripeptide-1, hexapeptide-12, hexapeptide-11, *Arnica montana* extract, *Ledum palustre*, or combinations thereof, in some embodiments, improve bruising. Lactoferrin is a plasmin inhibitor with high iron binding capacity and can aid in clearing lysed red blood cells and their constituents. Lactoferrin can block plasminogen activation on the cell surface by direct binding to human plasminogen, decreasing conversion to plasmin. Lactoferrin also has anti-microbial activity. See Zwirzitz A, Reiter M, Skrabana R, et al. Lactoferrin is a natural inhibitor of plasminogen activation. *Journal of Biological Chemistry.* 2018; 293(22):8600-8613.

Compositions as described herein, in some embodiments, improve bruising by improving healing or appearance of the bruise. In some embodiments, the compositions improve bruising by accelerating resolution of the bruise. For example, the compositions accelerate the transition of blue coloration to red coloration of the bruise. In some embodiments, improved appearance of the bruise comprises reduced size of the bruise. In some embodiments, improved appearance of the bruise comprises reduced discoloration of the skin. In some embodiments, improved appearance of the bruise comprises reduced swelling. In some embodiments, the compositions as described herein improve bruising by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein improve bruising by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Compositions described herein may improve bruising by improving macrophage function. In some embodiments, macrophage function comprises phagocytosis. In some embodiments, compositions as described herein improve macrophage phagocytosis by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, compositions as described herein improve macrophage phagocytosis by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Compositions and methods as described herein may result in elastin and/or collagen stimulation. Elastin is an assembly of microfibrils and tropoelastin (or soluble elastin). Elastin fibers are formed first by the synthesis of fibrillin microfibers which intertwine and then associate with tropoelastin (TE) protein molecules. TE molecules are bound together and cross linked together with fibrillin fibers by lysyl oxidase like enzyme 1 (LOXL1). The generated complex is then presented to the fibroblast by Fibulin 5 (FBLN5) which connects the complex to integrins that connect to the fibroblast. See Ashcroft, G. et al. Age-related Changes in the Temporal and Spatial Distributions of Fibrillin and Elastin mRNAs and Protein in Acute Cutaneous Wounds of Healthy Humans, Journal of Pathology. 1997; 183:80-89; Cenizo V, André V, Reymermier C, Sommer P, Damour O, E. P. LOXL as a target to increase the elastin content in adult skin: a dill extract induces the LOXL gene expression. *Experimental dermatology.* 2006; 15:574-581; Noblesse E, Cenizo V, Bouez C, et al. Lysyl oxidase-like and lysyl oxidase are present in the dermis and epidermis of a skin equivalent and in human skin and are associated to elastic fibers. *The Journal of investigative dermatology.* 2004; 122(3):621-630.

In some embodiments, elastin and/or collagen stimulation is a result of the compositions as described herein. In some embodiments, palmitoyl tripeptide-1 and palmitoyl hexapeptide-12 clear the extracellular matrix of aggregated fragmented collagen and elastin and then stimulate increased new collagen and elastin production. See Widgerow ΔD, Fabi S G, Palestine R F, et al. Extracellular Matrix Modulation: Optimizing Skin Care and Rejuvenation Procedures. *journal of drugs in dermatology.* 2016;15(4s):S63-S71; Widgerow A. TOPICAL SKIN RESTORATION TECHNOLOGY—ADVANCES IN AGE MANAGEMENT STRATEGIES. *MODERN AESTHETICS.* 2016(May/June): 1-8. In some embodiments, acetyl tetrapeptide-2 increases FBLN5 and LOXL1 protein levels, resulting in an increase in elastin synthesis. In some instances, acetyl tetrapeptide-2 upregulates genes related to Collagen 1 synthesis. Acetyl tetrapetide-2 can reduce parameters linked to skin flaccidity and dermal disorganization in vivo. See Product monograph: Uplevity™. Lipotec. June 2013.

In some embodiments, *Anethum graveolens* (dill extract) improves elastin and/or collagen stimulation by producing a reinduction of LOXL synthesis. See Cenizo V, André V, Reymermier C, Sommer P, Damour O, E. P. LOXL as a target to increase the elastin content in adult skin: a dill extract induces the LOXL gene expression. *Experimental dermatology.* 2006; 15:574-581. While microfibrils and soluble elastin continue to be synthesized throughout life, LOXL dramatically decreases from the age of 18. Increased levels of LOXL in the skin cause the assembly of microfibrils and tropoelastin, leading to improved mechanical properties of the skin. Id. Elastogenesis mainly occurs until the end of the second decade of the life, although the global content of skin elastin can increase after that, the nature of this elastin protein is often suboptimal and dysfunctional. See Ashcroft, G. et al. Age-related Changes in the Temporal and Spatial Distributions of Fibrillin and Elastin mRNAs and Protein in Acute Cutaneous Wounds of Healthy Humans, Journal of Pathology. 1997; 183:80-89. After this period, the elastin gene and fibrillin-1 gene are still active throughout the life although elastogenesis becomes low or inefficient. See Cenizo V, André V, Reymermier C, Sommer P, Damour O, E. P. LOXL as a target to increase the elastin content in adult skin: a dill extract induces the LOXL gene expression. *Experimental dermatology.* 2006; 15:574-581. LOXL, which declines after the first decades of life, has been shown to stimulate elastogenesis and maintain elastic fibers homeostasis. Id.; Noblesse E, Cenizo V, Bouez C, et al. Lysyl oxidase-like and lysyl oxidase are present in the dermis and epidermis of a skin equivalent and in human skin and are associated to elastic fibers. *The Journal of investigative dermatology.* 2004; 122(3):621-630; Liu X, Zhao Y, Gao J, et al. Elastic fiber homeostasis requires lysyl oxidase-like 1 protein. *Nat Genet.* 2004; 36(2):178-182. In some instances, dill extract increases the expression of LOXL in fibroblasts and in the skin engineering models and to de novo elastogenesis in vivo. See Cenizo V, André V, Reymermier C, Sommer P, Damour O, E. P. LOXL as a target to increase the elastin content in adult skin: a dill extract induces the LOXL gene expression. *Experimental dermatology.* 2006; 15:574-581.

In some embodiments, the compositions as described herein stimulate elastin production by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein stimulate elastin production by at least or about 0.5×, 1. OX, 1.5×, 2.0×, 2.5×, 3.0×, 3.5×, 4.0×, 5.0×, 6.0×, 7.0×, 8.0×, 9.0×, 10×, or more than 10×. In some embodiments, the compositions as described herein stimulate collagen production by at least or about 10%, 15%0, 20%, 25%, 30%, 35%, 40%, 45%, 50%, 55%, 60%, 65%, 70%, 75%, 80%, 85%, 90%, 95%, or more than 95%. In some embodiments, the compositions as described herein stimulate collagen production by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Compositions and methods as described herein, in some embodiments, simulate intrinsic hyaluronic acid (HA) production. Compositions and methods as described herein can improve high molecular weight HA penetration of the skin to the dermis. In some embodiments, compositions comprising hydroxymethoxyphenyl decanone, *Tremella fuciformis* extract, lactoferrin, sodium hyaluronate crosspolymer, phosphatidylserine, or combinations thereof stimulate intrinsic hyaluronic acid production.

In some embodiments, hydroxymethoxyphenyl decanone stimulates intrinsic hyaluronic acid production. Hydroxymethoxyphenyl decanone is a potent hyaluronic acid booster, antioxidant and anti-irritant and has been demonstrated to stimulate the dermal and epidermal hyaluronic acid level by 259% and 198% versus placebo, respectively in ex vivo human skin model. See Product monograph: Symdecanox, Symrise June 2015.

In some embodiments, *Tremella fuciformis* extract stimulates intrinsic hyaluronic acid production. In some embodiments, *Tremella fuciformis* provides high levels of moisture and anti-oxidant properties. See Li H, Lee H S, Kim S H, Moon B, Lee C. Antioxidant and anti-inflammatory activities of methanol extracts of *Tremella fuciformis* and its major phenolic acids. *J Food Sci.* 2014;79(4):C460-468; Liao W C, Hsueh C Y, Chan C F. Antioxidative activity, moisture retention, film formation, and viscosity stability of *Auricularia fuscosuccinea*, white strain water extract. *Biosci Biotechnol Biochem.* 2014; 78(6):1029-1036.

In some embodiments, sodium hyaluronate crosspolymer stimulates intrinsic hyaluronic acid production. Sodium hyaluronate crosspolymer is a chemically crosslinked hyaluronic acid derived from a non-animal source with high water-binding capacity. Sodium hyaluronate crosspolymer can function as a scavenger of damaging free radicals. Sodium hyaluronate crosspolymer comprises a gel structure with gel domains that hold tightly bound water, which can form a film on the skin and delivers water over time. In some embodiments, sodium hyaluronate crosspolymer comprises fifty (50) times the water binding capacity of hyaluronic acid.

In some embodiments, the compositions as described herein stimulate intrinsic hyaluronic acid production by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein stimulate intrinsic hyaluronic acid production by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Described herein are compositions and methods for stimulating adipogenesis. In some embodiments, fillers stimulate new adipose formation by mechanical stimulation of adipose stem cells in the dermal white adipose tissue layer. See Kruglikov I L, Wollina U. Soft tissue fillers as non-specific modulators of adipogenesis: change of the paradigm?*Experimental dermatology.* 2015; 24(12):912-915. In some embodiments, compositions comprising acetyl hexapeptide-38 stimulate adipogenesis. Hexapeptide-38 is a PGC1a stimulator (peroxisome proliferator-activated receptor-gamma-PPARγ-coactivator 1 alpha). PGC1a plays a central role in adipogenic activity. See Liang H, Ward W F. PGC-1alpha: a key regulator of energy metabolism. *Adv Physiol Educ.* 2006; 30(4):145-151. Compositions and methods as described herein may comprise a phospholipid delivery system to facilitate penetration and absorption of the materials through the stratum corneum. PGC1a strongly induces in differentiation of preadipocytes into white adipocytes under the influence of PPARγ. The young adipocytes formed under these conditions appear to be small and active, and this size and activity have been seen to be synergistic and in line with good elastin formation. See Ezure T, Amano S. Increment of subcutaneous adipose tissue is associated with decrease of elastic fibres in the dermal layer. *Exp Dermatol.* 2015; 24(12):924-929. As such, large, mature adipocytes have been associated with diminished elastin—manifesting as aged sagging skin—whereas younger, smaller, newly synthesized adipocytes are accompanied by increased elastin levels.

In some embodiments, the compositions as described herein stimulate adipogenesis by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein stimulate adipogenesis by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Described herein are compositions and methods resulting in reduced inflammation. Compositions and methods, in some embodiments, comprising phytoene, phytofluene, xylitol, or combinations thereof comprise anti-inflammatory effects.

In some embodiments, the compositions as described herein reduce inflammation by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein reduce inflammation by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Improvements in bruising, elastin and/or collagen simulation, hyaluronic acid stimulation, adipocyte stimulation, anti-inflammatory effects, or a combination thereof may be determined by comparison to a control. In some embodiments, the control is no treatment. In some embodiments, the control is vehicle treatment. In some embodiments, improvements are measured in a subject who received treatment with a composition described herein on a first portion of the body and vehicle or no treatment on a second portion of the body. For example, improvements are compared between a right arm that is treated with a composition as described herein and a left arm that received vehicle treatment.

Treatment Regimens

Compositions as described herein may be used with various treatment regimens. In some instances, the topical compositions described herein are administered or applied once per day, twice per day, three times per day or more. In some instances, the topical compositions described herein are administered or applied twice per day. The topical compositions described herein, in some embodiments, are administered or applied daily, every day, every alternate day, five days a week, once a week, every other week, two weeks per month, three weeks per month, once a month, twice a month, three times per month, or more. In some embodiments, the topical compositions described herein are administered or applied twice daily, e.g., morning and evening. In some embodiments, the topical compositions described herein are administered or applied for at least 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 12 months, 18 months, 2 years, 3 years, 4 years, 5 years, 10 years, or more. In some embodiments, the topical compositions described herein are administered or applied twice daily for at least or about 1 week, 2 weeks, 3 weeks, 1 month, 2 months, 3 months, 4 months, 5 months, 6 months, or more. In some embodiments, the topical compositions described herein are administered or applied once daily, twice daily, three times daily, four times daily, or more than four times daily for at least or about 1 week, 2 weeks, 3 weeks, 1 month, 2 months, 3 months, 4 months, 5 months, 6 months, or more.

In some embodiments, the compositions described herein are used in conjunction with a cosmetic procedure. In some embodiments, the cosmetic procedure comprises injection of a filler (e.g., hyaluronic acid filler).

Compositions as described herein when administered or applied prior to, during, or following injection of a filler (e.g., hyaluronic acid filler) may improve bruising, elastin and/or collagen simulation, hyaluronic acid stimulation, adipocyte stimulation, anti-inflammatory effects, or a combination thereof. In some instances, the compositions as described herein improve bruising, elastin and/or collagen simulation, hyaluronic acid stimulation, adipocyte stimulation, anti-inflammatory effects, or a combination thereof by 10%, 15%, 20%, 25%, 30%, 35%, 40%, 45%, 50%, 55%, 60%, 65%, 70%, 75%, 80%, 85%, 90%, 95%, or more than 95% as compared to a control. In some embodiments, the compositions as described herein improve bruising, elastin and/or collagen simulation, hyaluronic acid stimulation, adipocyte stimulation, anti-inflammatory effects, or a combination thereof by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×. In some embodiments, the compositions as described herein improve bruising, elastin and/or collagen simulation, hyaluronic acid stimulation, adipocyte stimulation, anti-inflammatory effects, or a combination thereof following 1 day, 2 days, 3 days, 4 days, 5 days, 6 days, 1 week, 2 weeks, 3 weeks, 1 month, 2 months, or more than 2 months following use of the compositions.

Compositions as described herein used in conjunction with injection of a filler (e.g., hyaluronic acid filler), in some embodiments, improve bruising, elastin and/or collagen simulation, hyaluronic acid stimulation, adipocyte stimulation, anti-inflammatory effects, or a combination thereof following the injection of the filler. In some embodiments, the compositions as described herein improve bruising, elastin and/or collagen simulation, hyaluronic acid stimulation, adipocyte stimulation, anti-inflammatory effects, or a combination thereof by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein improve bruising, elastin and/or collagen simulation, hyaluronic acid stimulation, adipocyte stimulation, anti-inflammatory effects, or a combination thereof by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

In some instances, the compositions described herein are administered or applied up to 1 day, up to 2 days, up to 3 days, up to 5 days, up to 6 days, up to 1 week, up to 2 weeks, up to 3 weeks, or more than 3 weeks prior to injection of a filler. In some instances, the compositions described herein are administered or applied immediately prior to injection of a filler (e.g., hyaluronic acid filler), up to 1 hour, up to 2 hours, up to 3 hours, up to 5 hours, up to 6 hours, up to 7 hours, up to 8 hours, up to 12 hours, up to 16 hours, up to 20 hours, or up to 24 hours prior to injection of a filler. Sometimes the compositions described herein are administered or applied singly, or over a time course, such as daily, multiple times weekly, weekly, biweekly, monthly or less frequently prior to injection of a filler. In some instances, the compositions described herein are administered or applied singly, or over a time course, such as daily, multiple times weekly, weekly, biweekly, monthly or more frequently prior to injection of a filler. In some embodiments, the compositions are topical compositions. In some instances, the topical compositions are administered or applied twice daily for at least or about 1 week, 2 weeks, 3 weeks, 1 month, 2 months, 3 months, 4 months, 5 months, 6 months, or more prior to injection of a filler. In some embodiments, the topical compositions described herein are administered or applied once daily, twice daily, three times daily, four times daily, or more than four times daily for at least or about 1 week, 2 weeks, 3 weeks, 1 month, 2 months, 3 months, 4 months, 5 months, 6 months, or more prior to injection of a filler.

In some instances, the compositions described herein are administered or applied up to 1 day, up to 2 days, up to 3 days, up to 5 days, up to 6 days, up to 1 week, up to 2 weeks, up to 3 weeks, or more than 3 weeks following injection of a filler (e.g., hyaluronic acid filler). In some instances, the compositions described herein are administered or applied immediately following injection of a filler, up to 1 hour, up to 2 hours, up to 3 hours, up to 5 hours, up to 6 hours, up to 7 hours, up to 8 hours, up to 12 hours, up to 16 hours, up to 20 hours, or up to 24 hours following injection of a filler. Sometimes the compositions described herein are administered or applied singly, or over a time course, such as daily, multiple times weekly, weekly, biweekly, monthly or less frequently following injection of a filler. In some instances, the compositions described herein are administered or applied singly, or over a time course, such as daily, multiple times weekly, weekly, biweekly, monthly or more frequently following injection of a filler. In some embodiments, the compositions are topical compositions. In some instances, the topical compositions are administered or applied twice daily for at least or about 1 week, 2 weeks, 3 weeks, 1 month, 2 months, 3 months, 4 months, 5 months, 6 months, or more following injection of a filler. In some embodiments, the topical compositions described herein are administered or applied once daily, twice daily, three times daily, four times daily, or more than four times daily for at least or about 1 week, 2 weeks, 3 weeks, 1 month, 2 months, 3 months, 4 months, 5 months, 6 months, or more following injection of a filler.

Stability Testing

Stability testing of the compositions can be conducted as follows.

High temperature testing is now commonly used as a predictor of long-term stability. High temperature testing can be conducted at 37° C. (98° F.) and 45° C. (113° F.). If a product is stored at 45° C. for three months (and exhibits acceptable stability) then it should be stable at room temperature for two years. A good control temperature is 4° C. (39° F.) where most products will exhibit excellent stability. Sometime, the product is also be subjected to –10° C. (14° F.) for three months.

In some instances, stability of the product is assessed by passing three cycles of temperature testing from –10° C. (14° F.) to 25° C. (77° F.). In such cases, the product is placed at –10° C. for 24 hours and then placed at room temperature (25° C.) for 24 hours. This completes one cycle. An even more rigorous test is a –10° C. to 45° C. five-cycle test. This puts emulsions under a tremendous stress.

The dispersed phase (of an oil-in-water emulsion) has a tendency to separate and rise to the top of the emulsion forming a layer of oil droplets. This phenomenon is called creaming. Creaming is one of the first signs of impending emulsion instability. A test method to predict creaming is centrifugation. Heat the emulsion to 50° C. (122° F.) and centrifuge it for thirty minutes at 3000 rpm. Then inspect the resultant product for signs of creaming.

Both formulas and packaging can be sensitive to the UV radiation. The product is placed in glass and the actual package in a light box that has a broad-spectrum output. Another glass jar completely covered with aluminum foil serves as a control. Discoloration of the product may be observed.

For all the above mentioned tests the color, odor/fragrance, viscosity, pH value, and, if available, particle size uniformity and/or particle agglomeration under the microscope can be observed.

Kits for Non-Invasive Use and Use with Invasive Procedures

Some embodiments of the methods and compositions provided herein include kits comprising peptides provided herein. In some embodiments, kits can be provided to an administering physician, other health care professional, a patient, or a caregiver. In some embodiments, a kit comprises a container which contains the peptide compositions in a suitable topical composition, and instructions for administering the peptide composition to a subject. The kit can optionally also contain one or more additional therapeutic or other agents. For example, a kit containing a peptide composition in topical form can be provided along with other skin care agents, such as, cleansers, occlusive moisturizers, penetrating moisturizers, sunscreens, sunblocks, and the like. The kit may contain the peptide composition in bulk form, or can contain separate doses of the peptide composition for serial or sequential administration or application. The kit can optionally contain one or more diagnostic tools, administration tools, and/or instructions for use. The kit can contain suitable delivery devices, such as, syringes, pump dispensers, single dose packets, and the like, along with instructions for administering the peptide compositions and any other therapeutic or beneficial agents. The kit can optionally contain instructions for storage, reconstitution (if applicable), and administration or application of any or all therapeutic or beneficial agents included. The kits can include a plurality of containers reflecting the number of administration or applications to be given to a subject, or the different products to be administered or applied to the subject.

In some embodiments, the composition is configured to support the skin before, during and after cosmetic procedures, and also works with the skin's own natural regenerating process and assists in improving the skin's appearance, and skin tightness. The topical composition can be applied immediately post-procedure for faster recovery, or generally for healthier looking skin. The composition can increase natural levels of elastin in the skin, improves the quality of existing elastin, stimulates increase in collagen production, and exhibits high antioxidant activity to reduce inflammation, redness and irritation. The topical composition is suitable for all skin types and post-procedure skin. The topical compositions can be provided to the patient in bulk form, to permit a suitable amount of the peptides to be self-administered by the patient. For example, the patient can apply an amount of the composition sufficient to provide an even coating over the affected area or as otherwise instructed by the physician. In certain embodiments it can desirable to incorporate additional therapeutic or active agents into the topical composition. Alternatively, adjunct therapies or agents can be administered or applied separately. For example, a cleanser, a sunblock, a sunscreen, a penetrating moisturizer, and/or an occlusive moisturizer can be provided for administration or application before or after the topical composition of the embodiments.

In one embodiment, a kit is provided for use in connection with a cosmetic skin procedure, as described herein. The kit may include a topical peptide composition, an occlusive moisturizer, a gentle cleanser, a penetrating moisturizer, and a broad spectrum SPF 30+ sunscreen.

The various examples of creams, ointments, lotions, solutions, gels, sprays and patches may incorporate the peptide compositions as described herein as the active ingredient, in combination with penetration enhancing agents and other active agents acting synergistically on the skin for the promotion of wound healing or wound closure or the treatment of chronic cutaneous wound.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Exemplary Compositions

An exemplary composition is seen in Table 1 and Table 2.

TABLE 1

| Ingredient | % by wt. |
| --- | --- |
| Butylene Glycol, Aqua, Acetyl Hexapeptide-38 | 0.05-1.25 |
| Xylitylglucoside, Anhydroxylitol, Xylitol | 0.2-5 |
| Water, Butylene Glycol, Arnica Montana Flower Extract | 0.1-2.5 |
| Glycerin, Palmitoyl Tripeptide-1 | 0.5-15 |
| Glycerin, Palmitoyl Hexapeptide-12 | 0.5-15 |
| Hexapeptide-11 | 0.001-0.025 |
| Sodium Hyaluronate Crosspolymer | 0.1-2.5 |
| Squalane, Dunaliella Salina Extract | 0.1-2.5 |
| Ledum Palustre (Labrador Tea) Extract, Radish Root Ferment Filtrate | 0.1-2.5 |
| Lactoferrin | 0.01-0.25 |

TABLE 1-continued

| Ingredient | % by wt. |
| --- | --- |
| Phosphatidylserine, Phospholipids, Tocopherol, Ascorbyl Palmitate | 0.02-0.5 |
| Aqua, Butylene Glycol, Peucedanum Graveolens (Dill) Extract, Xanthan Gum | 0.1-2.5 |
| Water, Tremella Fuciformis Sporocarp (Silver Ear Mushroom) Extract, Betaine, Glycerin | 0.1-2.5 |
| Propanediol, Lecithin | 0.4-10 |
| Caprylic/Capric Triglyceride, Hydroxymethoxyphenyl Decanone | 0.1-2.5 |
| Water, Acetyl Tetrapeptide-2, Caprylyl Glycol | 0.2-5 |
| Caprylic/Capric Triglyceride | 0.4-10 |
| Caprylyl Methicone | 0.1-2.5 |
| Water/Aqua/Eau | 40-90 |
| Phenoxyethanol, Ethylhexylglycerin | 0.17-4.25 |
| Polyacrylate-13, Polyisobutene, Polysorbate 20 | 0.5-12.5 |
| Caprylyl Glycol, Caprylhydroxamic Acid, Glycerin | 0.1-2.5 |
| Disodium EDTA | 0.02-0.5 |
| Propanediol | 0.04-1 |

TABLE 2

| Ingredient | % by wt. |
| --- | --- |
| Water/Aqua/Eau, | 50-95 |
| Glycerin | 0.5-9 |
| Caprylic/Capric Triglyceride | 1-9 |
| Propanediol | 0.01-5 |
| Polyacrylate-13 | 0.5-6 |
| Lactoferrin | 0.01-1 |
| Phosphatidylserine | 0.01-1 |
| Ledum Palustre (Labrador Tea) Extract | 0.1-2.5 |
| Arnica Montana Flower Extract | 0.0001-1 |
| Palmitoyl Hexapeptide-12 | 0.0001-1 |
| Palmitoyl Tripeptide-1 | 0.0001-1 |
| Hexapeptide-11 | 0.00500 |
| Acetyl Hexapeptide-38 | 0.0001-1 |
| Acetyl Tetrapeptide-2 | 0.0001-1 |
| Sodium Hyaluronate Crosspolymer | 0.0001-2.5 |
| Tremella Fuciformis Sporocarp (Silver Ear Mushroom) Extract | 0.001-2.5 |
| Peucedanum Graveolens (Dill) Extract | 0.01-2.5 |
| Hydroxymethoxyphenyl Decanone | 0.001-0.1 |
| Dunaliella Salina Extract | 0.001-0.5 |
| Betaine | 0.01-0.5 |
| Phospholipids | 0.01-1 |
| Xylitylglucoside | 0.1-2 |
| Squalane | 0.1-0.8 |
| Caprylyl Glycol | 0.1-0.5 |
| Anhydroxylitol | 0.1-1.5 |
| Polysorbate 20 | 0.01-0.5 |
| Xylitol | 0.1-0.5 |
| Butylene Glycol | 0.1-2 |
| Sorbitan Isostearate | 0.1-1 |
| Ethylhexylglycerin | 0.01-1 |
| Caprylhydroxamic Acid | 0.05-0.5 |
| Ascorbyl Palmitate | 0.001-0.1 |
| Xanthan Gum | 0.01-0.8 |
| Pentylene Glycol | 0.01-0.8 |
| Glucose | 0.01-0.8 |
| Helianthus Annuus (Sunflower) Seed Oil | 0.001-0.5 |
| Tocopherol | 0.001-0.8 |
| Leuconostoc/Radish Root Ferment Filtrate | 0.01-0.8 |
| Potassium Sorbate | 0.001-0.5 |
| Caprylyl Methicone | 0.1-0.8 |
| Polyisobutene | 0.1-.8 |
| Lecithin | 0.1-1 |
| Disodium EDTA | 0.1-1 |
| Phenoxyethanol | 0.1-2 |

Example 2. Clinical Evaluation of the Efficacy of a
Topical Product for the Treatment of Bruises Used
in Conjunction with Injection of a Filler
Comprising Hyaluronic Acid The objective of this study is to evaluate the efficacy of a
topical product comprising a formula as described in Table
1 or Table 2 in improving appearance of a bruise when
administered or applied before injection of a filler compris-
ing hyaluronic acid, after the injection of the filler, during the
injection of the filler, or combinations thereof.

The duration of the study is 3 months. Approximately 50
subjects will be enrolled. Subjects include healthy male and
female subjects 18 years of age or older. The inclusion
criteria and exclusion criteria are listed in Table 3.

TABLE 3

| Inclusion and Exclusion Criteria | |
| --- | --- |
| Inclusion Criteria | Age 18-60 years old male and female subjects electing to receive cosmetic injectables<br>Subjects are in good health<br>Subjects are willing to understand and provide informed consent |
| Exclusion Criteria | Pregnant or lactating<br>Subjects who in the Investigators opinion are not suitable for cosmetic injectables |

The study will consist of a Day 1 treatment visit and
follow-up visits on Days 2, 4, 6, 8, 10 and 14. Subjects may
consent for the study up to 30 days before Day 1.

The Day 1 procedures will consist of the following:
Completion of ICF, demographics, medical/dermatological
history. The subject will undergo injection a filler compris-
ing hyaluronic acid. A first set of subjects will have had
administration or application of the topical product prior to
injection of a filler comprising hyaluronic acid. A second set
of subjects will administer the topical product during injec-
tion of a filler comprising hyaluronic acid. A third set of
subjects will administer the topical product after injection of
a filler comprising hyaluronic acid. Standard photography
will be taken post bruise formation. Subjects will be ran-
domized to apply the topical bruise product on either the left
or right side of the face. Subjects will use the topical product
twice daily on the designated bruises.

Follow-up Days 2, 4, 6, 8, 10 and 14: The subject will
return to the clinic and be queried for any changes in health
status since the previous visit. Standardized photography
will be completed of the bruises.

Study measurements include efficacy and safety measure-
ments. Efficacy will be determined using standardized pho-
tography and the Subject Satisfaction Questionnaire. Stan-
dardized photos will be taken at every visit and post
procedure. These photos will be used for comparable assess-
ment of the bruises. Using the Subject Satisfaction Ques-
tionnaire, the subject will rate satisfaction with the product
and delivery. Safety measurements include recording
adverse events (AE) per the schedule of events.

Study efficacy is determined using primary efficacy end-
points and secondary efficacy endpoints. Primary efficacy
endpoints include Global Improvement in the treated bruises
compared to the non-treated. Secondary efficacy endpoints
include Subject Satisfaction Questionnaire at end of study.
Safety endpoints are also measured as incidence (severity
and causality) of any local and systemic adverse events
(AEs).

While preferred embodiments of the present disclosure
have been shown and described herein, it will be obvious to
those skilled in the art that such embodiments are provided
by way of example only. Numerous variations, changes, and
substitutions will now occur to those skilled in the art
without departing from the disclosure. It should be under-
stood that various alternatives to the embodiments of the
disclosure described herein may be employed in practicing
the disclosure. It is intended that the following claims define
the scope of the disclosure and that methods and structures
within the scope of these claims and their equivalents be
covered thereby.

What is claimed is:

1. A method for improving bruising, stimulating
hyaluronic acid production, stimulating elastogenesis,
stimulating collagenesis, or stimulating adipogenesis in a
subject, the method comprising:
   applying to a body region or a target area of the subject
      a topical composition comprising:
      one or more ingredients encapsulated in a liposome;
      a tripeptide-1; and
      a hexapeptide-12,
   wherein the topical composition is administered or
      applied before a cosmetic procedure, after the cosmetic
      procedure, during the cosmetic procedure, or combi-
      nations thereof, and
   wherein the cosmetic procedure comprises injection of a
      filler.

2. The method of claim 1, wherein the topical composition
is administered or applied at least 1 day prior to the cosmetic
procedure.

3. The method of claim 1, wherein the topical composition
is administered or applied at least 1 day after the cosmetic
procedure.

4. The method of claim 1, wherein the filler comprises
hyaluronic acid.

5. The method of claim 1, wherein the body region
comprises an upper lip, a lower lip, a mouth, a cheek, a chin,
a hand, a temple, or a peri-ocular region.

6. The method of claim 1, wherein the target area com-
prises a wrinkle, an oral commissure, a marionette line, a
mandibular hollow, raised jowls, a frowning mouth, a pouty
lower lip, a lateral expression line, a mental crease, a chin
dimpling, a zygomatic hollow, a nasolabial fold, a tear
trough, or a brow lift.

7. The method of claim 1, wherein the tripeptide-1 is
present in the composition at 1-10 ppm.

8. The method of claim 1, wherein the hexapeptide-12 is
present in the composition at 1-10 ppm.

9. The method of claim 1, wherein hexapeptide-11 is
present in the composition at 50-150 ppm.

10. The method of claim 1, wherein the composition
further comprises a tetrapeptide-2.

11. The method of claim 1, wherein the composition
further comprises phosphatidylserine.

12. The method of claim 1, wherein the composition
further comprises lactoferrin.

13. The method of claim 12, wherein the lactoferrin is
encapsulated in a liposome.

14. The method of claim 1, wherein the composition
further comprises a hexapeptide-38.

15. The method of claim 14, wherein the hexapeptide-38
is encapsulated in a liposome.

16. The method of claim 1, wherein the composition
further comprises *Ledum palustre* extract, dill extract, *Tre-
mella fuciformis* extract, butylene glycol, glycerin, squalane,
*Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, sodium hyaluronate crosspolymer, xylitylglucoside, anhydroxylitol, xylitol, hydroxymethoxyphenyl decanone, or combinations thereof.

17. The method of claim 1, wherein the composition improves macrophage function.

18. The method of claim 1, wherein the composition stimulates at least one of the following:

elastogenesis, collagenesis, or both, by inducing LOXL gene expression; or intrinsic hyaluronic acid production.

\* \* \* \* \*